(12) United States Patent
Rosen

(10) Patent No.: US 9,144,381 B2
(45) Date of Patent: Sep. 29, 2015

(54) MOBILE SELF-MANAGEMENT COMPLIANCE AND NOTIFICATION METHOD, SYSTEM AND COMPUTER PROGRAM PRODUCT

(75) Inventor: Howard Rosen, Toronto (CA)

(73) Assignee: LifeWIRE Corporation, Toronto, Ontario (CA)

( * ) Notice: Subject to any disclaimer, the term of this patent is extended or adjusted under 35 U.S.C. 154(b) by 699 days.

(21) Appl. No.: 11/616,783

(22) Filed: Dec. 27, 2006

(65) Prior Publication Data

US 2007/0179355 A1     Aug. 2, 2007

Related U.S. Application Data

(60) Provisional application No. 60/754,603, filed on Dec. 30, 2005.

(51) Int. Cl.
    *A61B 5/00*            (2006.01)
    *G06F 19/00*         (2011.01)
    *A61B 5/02*            (2006.01)
    *A61B 5/145*          (2006.01)

(52) U.S. Cl.
CPC .......... *A61B 5/0002* (2013.01); *G06F 19/3406* (2013.01); *A61B 5/02* (2013.01); *A61B 5/14532* (2013.01); *G06F 19/322* (2013.01); *G06F 19/324* (2013.01); *G06F 19/36* (2013.01)

(58) Field of Classification Search
CPC .............. G06F 19/3481; G06F 19/363; G06F 19/3456; G06F 19/3475; G06F 19/324; G06F 19/3406; G06F 19/3418; G06F 19/321; G06F 19/322; G06F 19/325; G06F 19/327; G06F 19/3431; G06F 19/345; A61B 5/002; A61B 5/0022; A61B 5/021; A61B 5/02055; A61B 5/0402; A61B 5/053; A61B 5/4866; A61B 5/0031; A61B 5/0476; A61B 5/0537; A61B 5/0538; A61B 5/08; A61B 5/11; A61B 5/1118; A61B 5/165; A61B 5/02; A61B 5/14532; A61B 5/0002; G01G 19/4146; G01G 23/3735; G01G 23/3742; G01G 19/44; G06Q 50/22; G06Q 50/24; G06Q 10/109; G06Q 30/02; G06Q 30/0601; G06Q 50/20; H04W 4/00
USPC ............................................... 600/300; 3/300
See application file for complete search history.

(56) References Cited

U.S. PATENT DOCUMENTS

| | | | | |
|---|---|---|---|---|
| 4,821,027 A | * | 4/1989 | Mallory et al. | 340/521 |
| 5,935,060 A | * | 8/1999 | Iliff | 600/300 |
| 6,022,315 A | * | 2/2000 | Iliff | 600/300 |
| 6,270,456 B1 | * | 8/2001 | Iliff | 600/300 |
| 6,494,830 B1 | * | 12/2002 | Wessel | 600/300 |

(Continued)

*Primary Examiner* — William Thomson
*Assistant Examiner* — Shirley Jian
(74) *Attorney, Agent, or Firm* — Finnegan, Henderson, Farabow, Garrett & Dunner LLP

(57) ABSTRACT

A remote interactive method, system and computer program product is provided for self-managing a person's regular lifestyle needs through controlled notification and feedback. The invention provides a simple, cost effective and flexible self-management and compliance scheme that does not require third party intervention or treatment options typical with immediate-response or alert-based systems. The invention also provides for long term management and analysis for the benefit of the individual. In implementing the invention in a healthcare environment, the individual will gain a better understanding of managing their lifestyle and behaviour. A related business model is also disclosed.

28 Claims, 17 Drawing Sheets

(56) References Cited

U.S. PATENT DOCUMENTS

| | | | |
|---|---|---|---|
| 6,535,294 B1* | 3/2003 | Arledge et al. | 358/1.15 |
| 6,641,532 B2* | 11/2003 | Iliff | 600/300 |
| 6,980,999 B1* | 12/2005 | Grana | 600/300 |
| 7,090,638 B2* | 8/2006 | Vidgen | 600/300 |
| 7,344,496 B2* | 3/2008 | Iliff | 600/300 |
| 7,361,143 B2* | 4/2008 | Kirchhoff et al. | 600/300 |
| 8,032,397 B2* | 10/2011 | Lawless | 705/3 |
| 8,337,409 B2* | 12/2012 | Iliff | 600/483 |
| 2003/0083556 A1* | 5/2003 | Cosentino et al. | 600/300 |
| 2003/0229514 A2* | 12/2003 | Brown | 705/2 |
| 2004/0030918 A1* | 2/2004 | Karamchedu et al. | 713/200 |
| 2004/0122702 A1* | 6/2004 | Sabol et al. | 705/2 |
| 2005/0038326 A1* | 2/2005 | Mathur | 600/300 |
| 2005/0113650 A1* | 5/2005 | Pacione et al. | 600/300 |
| 2006/0248183 A1* | 11/2006 | Barton | 709/224 |
| 2007/0168228 A1* | 7/2007 | Lawless | 705/2 |

* cited by examiner

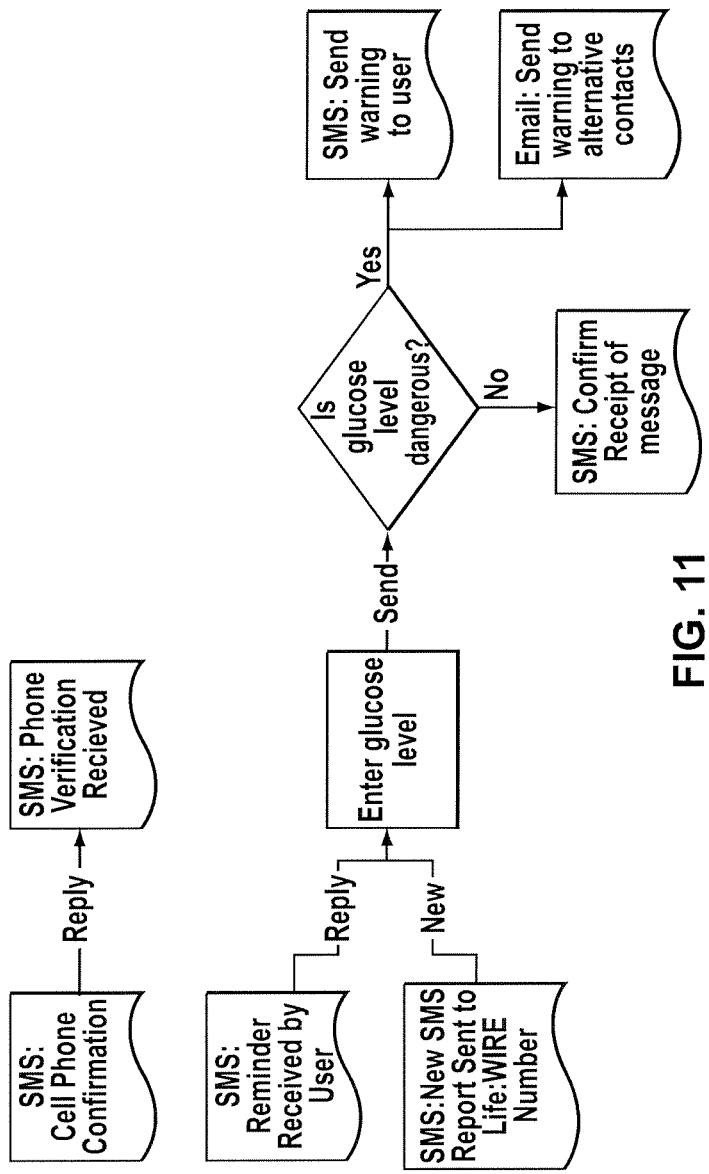

MOBILE SELF-MANAGEMENT COMPLIANCE AND NOTIFICATION METHOD, SYSTEM AND COMPUTER PROGRAM PRODUCT

This application claims the benefit of U.S. Provisional Application No. 60/754,603 filed Dec. 30, 2005.

FIELD OF THE INVENTION

The present invention relates to communication systems for user compliance and monitoring. More particularly, the present invention relates to interactive communication systems for the compliance and monitoring health. The present invention further relates to a method of generating revenue for an interactive communication system for compliance and monitoring health.

BACKGROUND OF THE INVENTION

For patients suffering from chronic illness, monitoring of their condition and ensuring compliance of health regimes is vital to their long term health. Often patients are not successful at keeping proper records of health statistics related to their condition. Logbooks, PDAs and computers adapted to monitor their conditions often become a burden, furthering their suffering instead of being a tool to assist them in effectively dealing with their condition.

In general, the ability to ensure the monitoring and response to changing physiological conditions in real time gives the patient the ability to react to their condition before an emergency occurs. The improved care through direct patient management means reduced costs associated with chronic conditions: less physician visits, less hospital visits and fewer sick days. It is documented that patient are up to 90% more compliant in reporting data using electronic diaries (eDiaries) versus paper based systems.

Diabetes is an example of a particularly difficult chronic condition requiring constant monitoring and attention by the patient. Diabetes is associated with an increased risk for a number of serious, often life-threatening complications and certain groups may experience an even greater threat. There are currently approximately 20 million people in North America alone suffering from Diabetes; this number is estimated to climb to 45 million by 2010. Good diabetes management can help reduce risk. However, approximately 70% of Diabetics do not manage their disease. In recent report issued by the American Association of Clinical Endocrinologists (AACE) entitled the "State of Diabetes in America", blood sugar control across the United States was examined. The findings revealed that approximately two out of three Americans with type 2 diabetes analyzed in the study did not reach the AACE-recommended target blood sugar goal in 2003 and 2004.

Further, studies in the United States and abroad have found that improved glycemic control benefits people with either type 1 or type 2 Diabetes. In fact, after a 17 year federal study, the New England Journal of Medicine reported in the Dec. 22, 2005 issue that "intense control of blood sugar prevents heart attacks and strokes by nearly 50%". According to the American Diabetes Association, every percentage point drop in A1C blood test results (e.g., from 8.0% to 7.0%) reduces the risk of microvascular complications (eye, kidney, and nerve diseases) by 40%.

In addition to glucose monitoring and control, blood pressure control reduces the risk of cardiovascular disease (heart disease or stroke) among persons with diabetes by 33% to 50%, and the risk of microvascular complications (eye, kidney, and nerve diseases) by approximately 33% [American Diabetes Association]. In general, for every 10 mm Hg reduction in systolic blood pressure, the risk for any complication related to diabetes is reduced by 12%. The control of blood lipids also is important, with studies showing that improved control of cholesterol or blood lipids (for example, HDL, LDL, and triglycerides) can reduce cardiovascular complications by 20% to 50%.

In addition to those suffering from chronic disease, preventative medicine often requires the monitoring of specific health-related statistics. For example, the monitoring of blood pressure and cholesterol is necessary for many people, especially those with a family history of cardiac problems. Moreover, so-called "pre-diabetics" are advised to keep close watch on their glucose level as a preventative measure in avoiding the full blown disease.

There have been various systems proposed for health monitoring. For example, U.S. Pat. No. 6,656,114 to Poalsen et al. discloses a specific method of self treating a disease, such as diabetes, wherein data is collected and processed to provide a number of alternative treatment options based on the analysis. The method and system is dependent on the diabetic patient to input the relevant data for analysis and treatment options. Specialized hardware is disclosed, namely a functional master module, providing a displaying means and input means, and includes a doser with transmitting and receiving capabilities.

U.S. patent application No. 2004/0059599 to McIvor discloses a health system and method to facilitate monitoring and management by a healthcare provider. The patient is prompted for various health-related data, which is then forwarded to the healthcare provider. The system is an acute health management system, requiring a response to an "alert" from the patient and subsequently provides options for alternative treatments.

U.S. Pat. No. 6,728,341 to Puchek et al. discloses a response and alert system supervised by a caregiver wherein the caregiver monitors the acute responses of the supervised person.

U.S. patent application No. 2004/0054263 to Moerman et al. discloses a specific diabetic monitoring and treatment system of a patient requiring a counselling centre, a glucometer, and a communication device adaptive thereof. The counselling centre requires a healthcare professional to provide advice, treatment options and coaching.

Although there are many alert type systems that have been developed, a major issue is the compliance element in being able to determine or enable greater compliance by ensuring that patients are acting in compliance with their respective health regimes. Although this may include measurements such as glucose levels or blood pressure, it may also require the taking of one or more medications, as well as elements such as exercise, discomfort levels or simply how the individual is feeling.

On the basis of the foregoing, there is a need for an interactive lifestyle monitoring system that is mobile and has a self-management aspect. There is a further need for an interactive lifestyle compliance and monitoring system that is simple, cost-effective, flexible, and requires no specialized hardware. There is yet a further need for an interactive lifestyle monitoring system that does not require third party intervention.

SUMMARY OF THE INVENTION

The present invention is a remote interactive method, system and computer program product for self-managing a person's regular lifestyle needs and attributes through a controlled notification and feedback system that monitors and ensures compliance.

In one embodiment, the system includes an input device comprising a communication means, a set-up means, a set-up notification means, an approval means, and a notification and data analysis means. The system furthermore comprises a user and administrator back-end means which includes a compliance measurement means.

The system provides for feedback and measurement for healthcare provides to ensure that those under their care are complying with notifications and respective regimes.

In that regard, the invention involves three compliance related elements: (i) relating to the direct management with a user; (ii) monitoring such compliance; and (iii) on the business model, creating an incentive for the user to use the invention over and above health concerns.

The system and method provides a simple, cost effective, and flexible self-management that does not require a third party intervention or treatment options on an immediate response or alert based system. The system provides for a long term management, compliance and analysis for the benefit of the individual. In implementing this method in a healthcare environment, the individual will gain a better understanding of managing their lifestyle and behaviour and allow for healthcare managers to measure compliance of certain activities (if required). Further, employing already existing and available low cost technology improves the rate of patient data capture.

Whereas the prior art has involved the intervention of a third party in the monitoring process (whether a healthcare provider, family member or otherwise), the present invention provides for self-management. Self-management provides a reinforcement mechanism that allows the patient to remain proactive and positive in relation to their condition.

Users are responsible for tailoring the setup to their particular needs. Notifications (such as a reminder or an alert) are provided on a regularly basis, prompting users to take necessary quantitative or qualitative measurements, medication, or to record particular activities or conditions. These notifications can be tailored in a number of ways, in accordance with the present invention. For example, the users can choose to monitor the particular attribute or attributes that are relevant to their condition, including glucose level, temperature, blood pressure, heart rate, weight, medication intake, pain characteristics, etc. The user is able to choose the number of notifications, and schedule them appropriately. The system confirms the input from the user, resulting in a reduction in the possibility of error. Such input in monitored, allowing the ability to ensure compliance or to determine the extent of compliance of the user.

The present invention utilizes SMS ("Short Message Service") and MMS ("Multimedia Message Service") technology with ordinary cellular phones or other personal communication devices. The present invention is advantageous in this respect, since it relies on existing SMS/MMS telecommunication technology and technology owned by the user, and not specialized hardware. However, the phone is not the only means of data entry; information can be entered into the system via an Internet portal. The system comprises two separate interfaces in this respect: (i) a consumer interface; and (ii) a system administrator interface.

The user is prompted for information, e.g., notification attributes, and the information is submitted back to the server. Based on disease-specific protocols determined by the user, the data can be analyzed immediately to identify trends, especially the detection of worsening conditions. Based on user-configured rules, family and other care-givers can be notified immediately of any adverse trends.

Users and their healthcare network can access more detailed information regarding the data collected through a web interface. The raw input data, basic trends and charts show the patients' most recent information as well as historical information which can all be printed out. Analytical tools can also be created and linked with the database. In addition, the healthcare provider and/or caregiver can also, based on the information, 'push' key messages via the present invention to a user or group of users depending on the circumstances.

The present invention also contemplates the pairing of other hardware, apart from personal communication devices, with the notification and feedback means. For example, patients can link "smart" BLUETOOTH™ enabled glucometers directly with the system or similar 'smart' monitors relating to measurements such as blood pressure, heart rate or even distance run. Furthermore, a global positioning device could be linked with the system or within the communication device to provide an advantageous feature if patient location monitoring is desired or analytics as to past or future location related behaviour. Hardware can also be adapted within the communication device such as biometric sensors to allow for quantitative measurements of the various attributes.

The present invention is preferably employed to provide monitoring and compliance systems for patients suffering from Diabetes, with the input data being related to glucose levels and/or blood pressure information. The present invention contemplates the monitoring of a plurality of measurements as opposed to just a single measurement. For example, Diabetes-related monitoring can consist of glucose levels, blood pressure values, heart rate, temperature, etc., or compliance issues such as whether medication has been taken and whether a user has exercised as may be required. It is to be expressly understood that monitoring of Diabetes-related conditions is only an example of an implementation, and the present invention contemplates various other applications, as discussed herein.

In an aspect of the present invention, the monitoring system is employed to monitor the blood pressure data of a user. In a further aspect of the present invention, the monitoring system can be used to track multiple measurements for patients who have undergone organ transplant. The present invention can also be employed to monitor a patient's thyroid condition, or to track Alzheimer's sufferers, or used to determine the mobility status of Arthritis sufferers, or as a means to record and monitor the medication intake and compliance for anyone on a specific medication regiment. The present invention is also well-suited for both diet management and related analysis, and exercise management and related analysis.

Further, the present invention is also operable to prompt the user for specific non-quantitative health or lifestyle related information related to any of the applications discussed herein.

In further aspects of the present invention, the monitoring system can be utilized for specific non-health related purposes, including but not limited to the following: maintaining contact with children; maintaining conduct with adults requiring supervision, such as with prison inmates, people involved in extreme-style sports such as skiing or cross country running, walkers, joggers, bike riders, etc.; meeting notification; reminder notification; travel or location updates (i.e. for people keeping track of travelers, such as children); fleet attributes such as gas consumption (input of fuel used and distance traveled); any type of location/trend analysis, including trend analysis involving a combination of location/activity and other data (e.g., tracking activity with glucose level or blood pressure); general remote input of an activity on a regular basis and analyzed for access by user and approved user(s); and/or general notification reminder system based on pre-determined parameters.

In yet a further aspect of the present invention, the present invention is adaptable to a business model whereby revenue is generated from the collection of service fees.

BRIEF DESCRIPTION OF THE DRAWINGS

A detailed description of the preferred embodiments is provided herein below by way of example only and with reference to the following drawings, in which:

FIG. 10 is a flowchart illustrating a further aspect of one particular embodiment of the present invention, namely database schema requirements for the blood sugar report management system depicted in FIG. 9.

FIG. 11 is a flowchart illustrating a further aspect of one particular embodiment of the present invention, namely a mobile reporting system.

FIG. 12 is a flowchart illustrating a further aspect of one particular embodiment of the present invention, namely database schema requirements for the mobile reporting system depicted in FIG. 11.

Figure 1A:
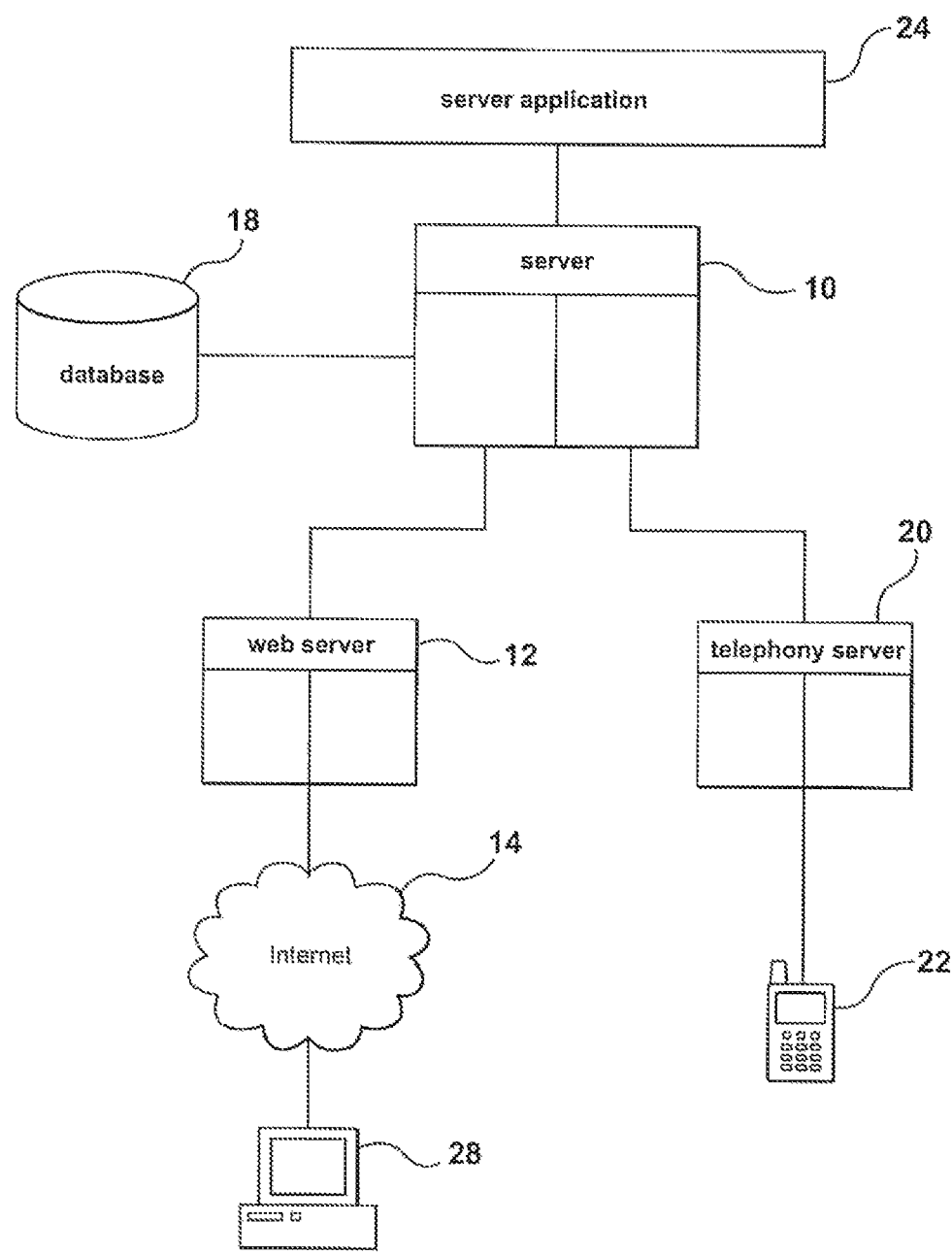
FIG. 1A is a system diagram of the present invention, in one particular embodiment thereof.

In the drawings, one embodiment of the invention is illustrated by way of example. It is to be expressly understood that the description and drawings are only for the purpose of illustration and as an aid to understanding, and are not intended as a definition of the limits of the invention.

DETAILED DESCRIPTION OF THE INVENTION

Note that the term "Life:WIRE" is used herein for a method and system in accordance with the present invention.

With reference to FIG. 1A, the system of the present invention is best understood as a server (10) (referred to as the intermediary server computer) or group of interconnected servers and associated utilities. The server (10) in one particular embodiment of the present invention includes a web server (12) connected to the Internet (14), and operable to provide a series of web pages (not shown) further described below. The server (10) is also connected to a database (18).

In an embodiment of the present invention, the personal communication device (22) consists of a cellular phone, as illustrated in FIG. 1A, in which case the telephony server (20) of the present invention is further operable to support a connection between the communication device (22) and the server (10).

Figure 1B:
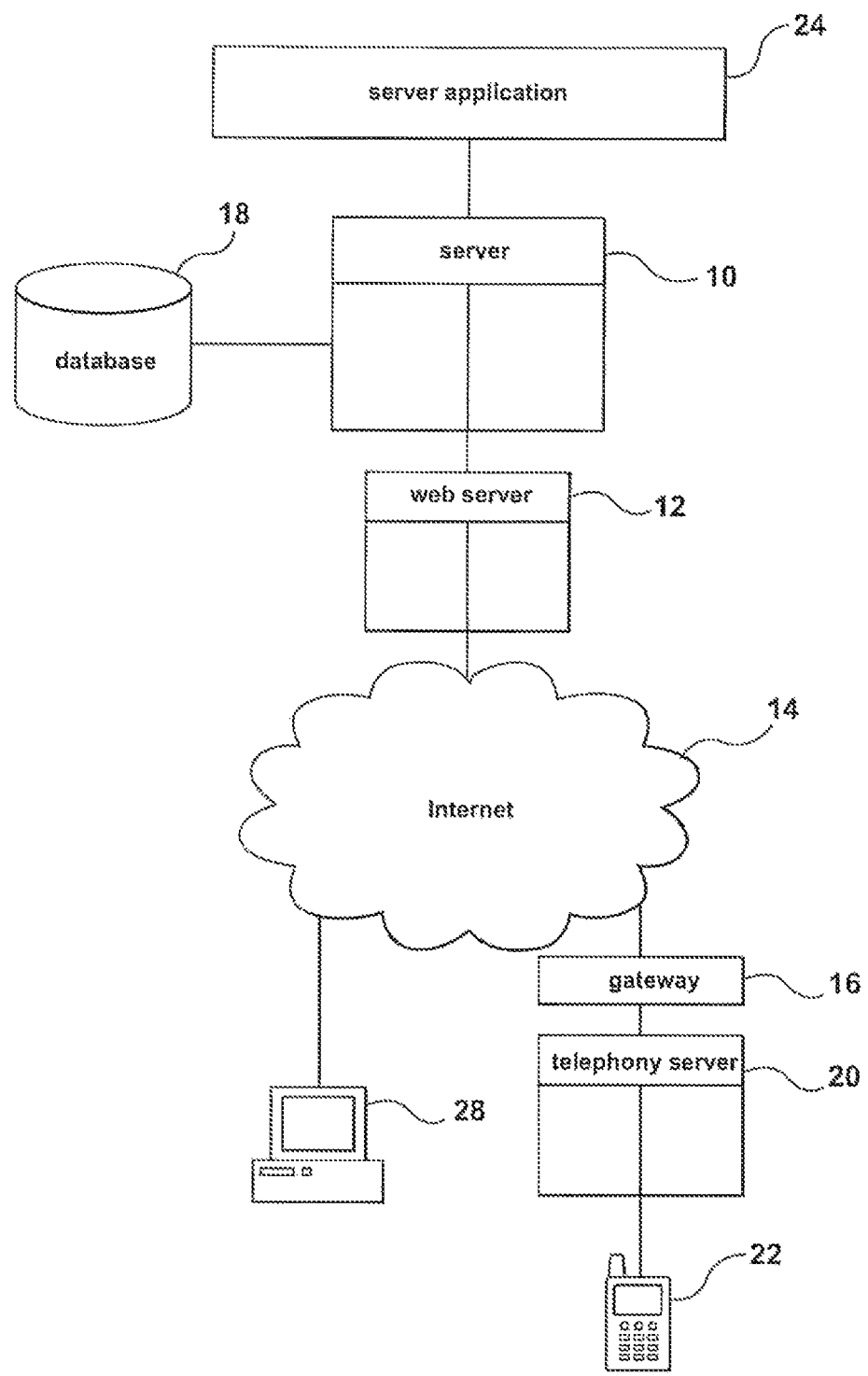
FIG. 1B is a system diagram of the present invention, in another embodiment thereof.

Alternatively, it should be understood that the telephony server (20) can support the connection between the communication device (22) and the server (10) via the Internet (14) through a wireless gateway (16). This embodiment is illustrated in FIG. 1B.

A server application (24) is linked to the server (10) of the present invention. The server application (24) consists of one or more software utilities that enables the described processing steps and supports the described functions, in accordance with the present invention. The computer program of the present invention is therefore best understood as the server application (24) linked to server (10). It should be understood that one of the aspects of the present invention is that there is no requirement for any specific programming on the communication device (22).

Suitable communication interfaces (not shown) are provided to the various components of server (10) in a manner that is known to enable the various communications there between.

Figure 2A:
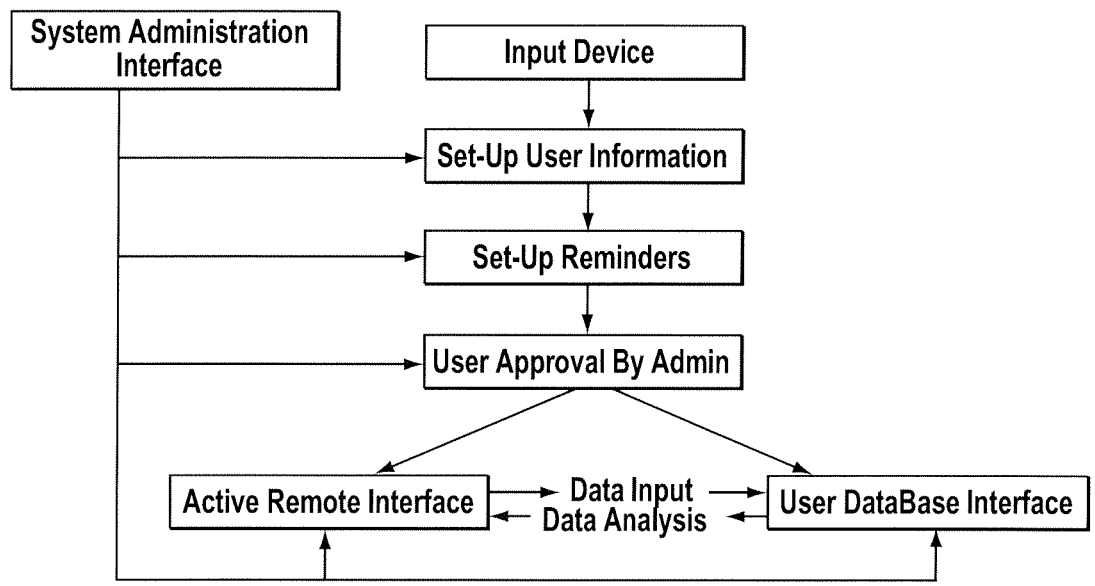
FIG. 2A is a flowchart illustrating the overall method of the present invention.

The overall method of the present invention is illustrated in FIG. 2A. In summary, the method of the present invention consists of: (A) a user using an input device as a communication means; (B) the user sets-up an account and specifies a lifestyle notification scheme; (C) the account is approved by an administrator; (D) notifications (a notification can be an alert or a reminder, for example, depending on the implementation) are provided to user in accordance with their setup and user provides information to the system; (E) users' response data is analysed. The present invention further comprises both a user and administrator interfaces.

In a particular implementation of the present invention, related set-up functions and routines are initiated from one or more personal computers (28) that communicate with the web server (12) via the Internet (14). A user, using a personal computer (28), is first required to sign up to a website associated with the web server (12) and to perform certain set-up functions related to the operation of the present invention. The user sets up an account that is password protected. The user then determines the number of daily notification reminders, which can range from one to six, for example. Although the description herein discusses the frequency of notifications as within one to six per day, it should be understood that the present invention is not limited in this regard. The optimal number of notifications for any given user will vary, and may be greater than six per day or less than one per day.

The user also determines whether they want SMS notification to be sent to their cellular phone, for example, or alternatively the user can select strictly "active" interaction, meaning that the system of will anticipate Internet-only input and there is no requirement for SMS notification.

The input to the cellular phone (22) can be via simple text entry using the keypad, or the device can be configured to operate in a voice-activated manner. If voice-activated, the notifications would have an additional confirmation step whereby it would confirm the accuracy of the information entered by the user. The present invention contemplates the use of personal communication devices that provide technological means to measure and health or lifestyle related information of the user and subsequently communicate the information. As an example, "smart glucometers" can be employed by the user to reply to notifications by communicating glucose levels in accordance with the present invention. Other advanced personal communication devices can be employed having the capabilities to take a user's temperature, measure blood pressure, heart rate, etc. Furthermore, sensors can be embedded into the personal communication device such as a cell phone that can quantitively measure attributes such as temperature, heart rate, etc.

The user selects the interval time period to which the trend analysis is conducted by the system. As a default, trend analysis is conducted for every ten measurements, for example. The user also determines and selects the parameters for the trends in terms of when to issue notifications. The user specifies who, if anyone, should be sent an alert or notification when said notification parameters are met.

Figure 2B:
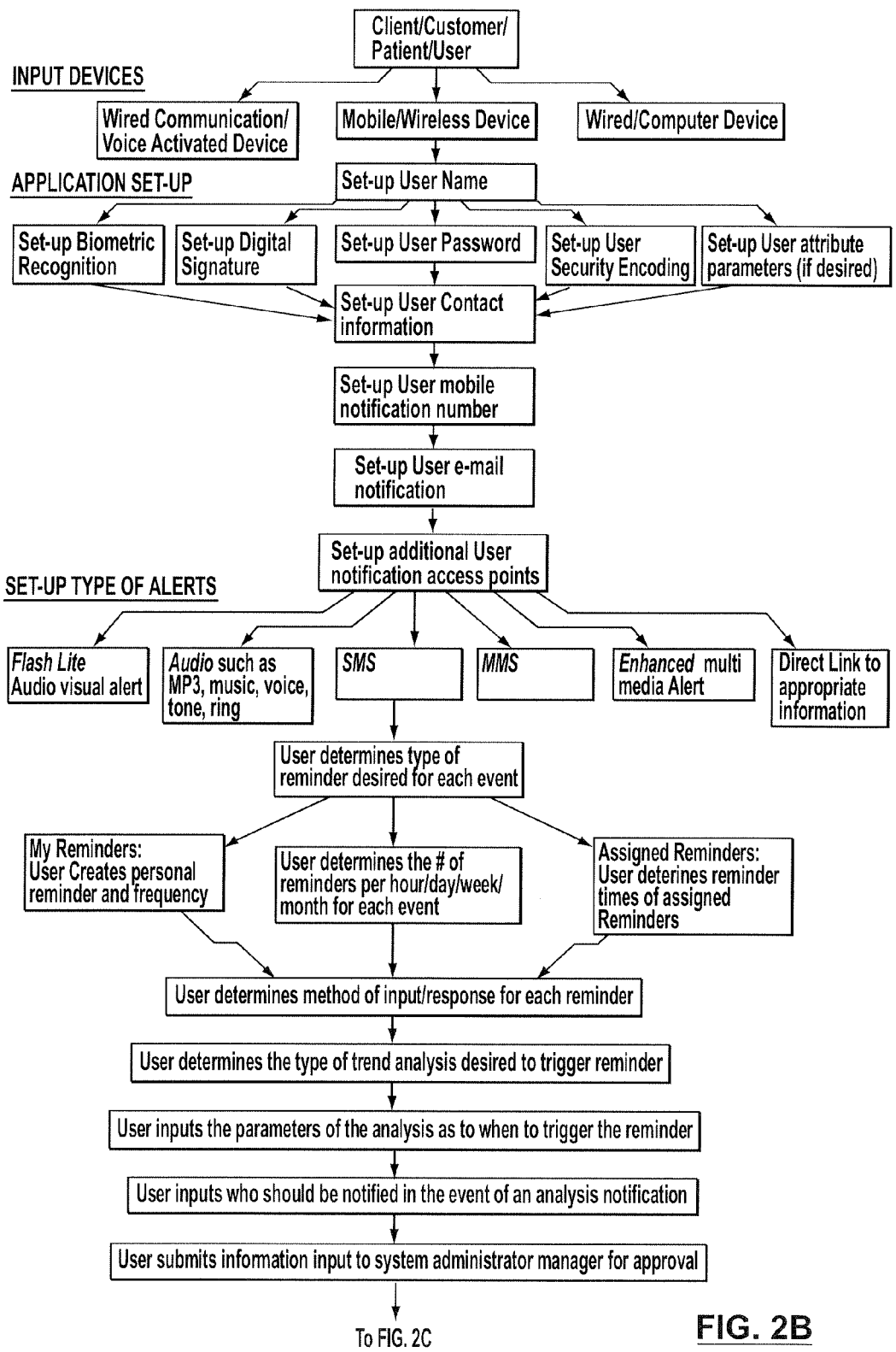
FIG. 2B is a flowchart illustrating aspects of the method illustrated in FIG. 2A, namely the user's set-up, and the user's notification set-up.

FIG. 2B depicts further aspects of the present invention. The user uses one or more of the input devices to provide the required information to accomplish the application set-up. The application set-up involves inputting information relating to the user. Included in the application set-up are attribute parameters, if desired, which are elements that would allow Life:WIRE to better assign questions/notifications worded in a matter most likely preferable to the user. It would also Life:WIRE to group the user with similar attributes for chats, support, etc. The user thus establishes the notification scheme based on their own interactive lifestyle monitoring needs.

The notifications are also set-up, and there is a plurality of notification or alert types, as depicted. The notifications can be set-up in a plurality of ways, for example, single query, multiple query with no immediate response required, or multiple query with a response dependent on input. The user may determine the nature of the one or more elements measured or may be pre-determined by a third party administrator for the user. In addition, a user may desire notifications for multiple events (e.g., glucose, blood pressure, etc.). A user may also specify that the wish to response via alternate means than used to remind (e.g., SMS notification but a response via computer). The parameters for analysis for triggering the notification (i.e. a reminder or an alert) can be established either by the user or by a third party administrator.

Figure 2C:
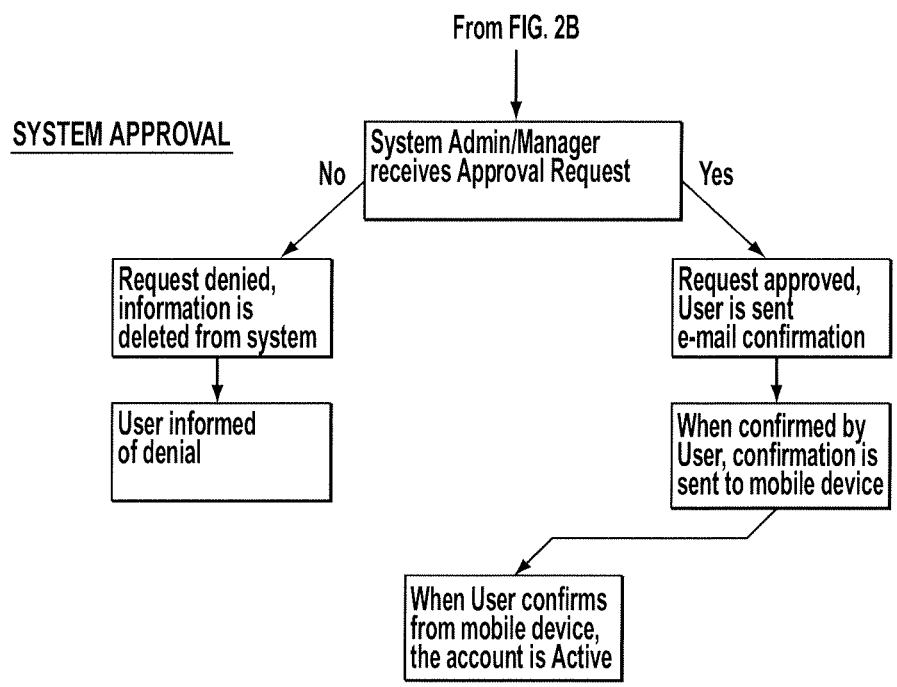
FIG. 2C is a flowchart illustrating aspects of the method illustrated in FIG. 2A, namely system/admin approval.

Further, there is a system approval aspect as shown in FIG. 2C. In the approval process, the user submits all relevant and required information to a system administrator or manager for approval, and they determine whether an account is activated.

Figure 3:
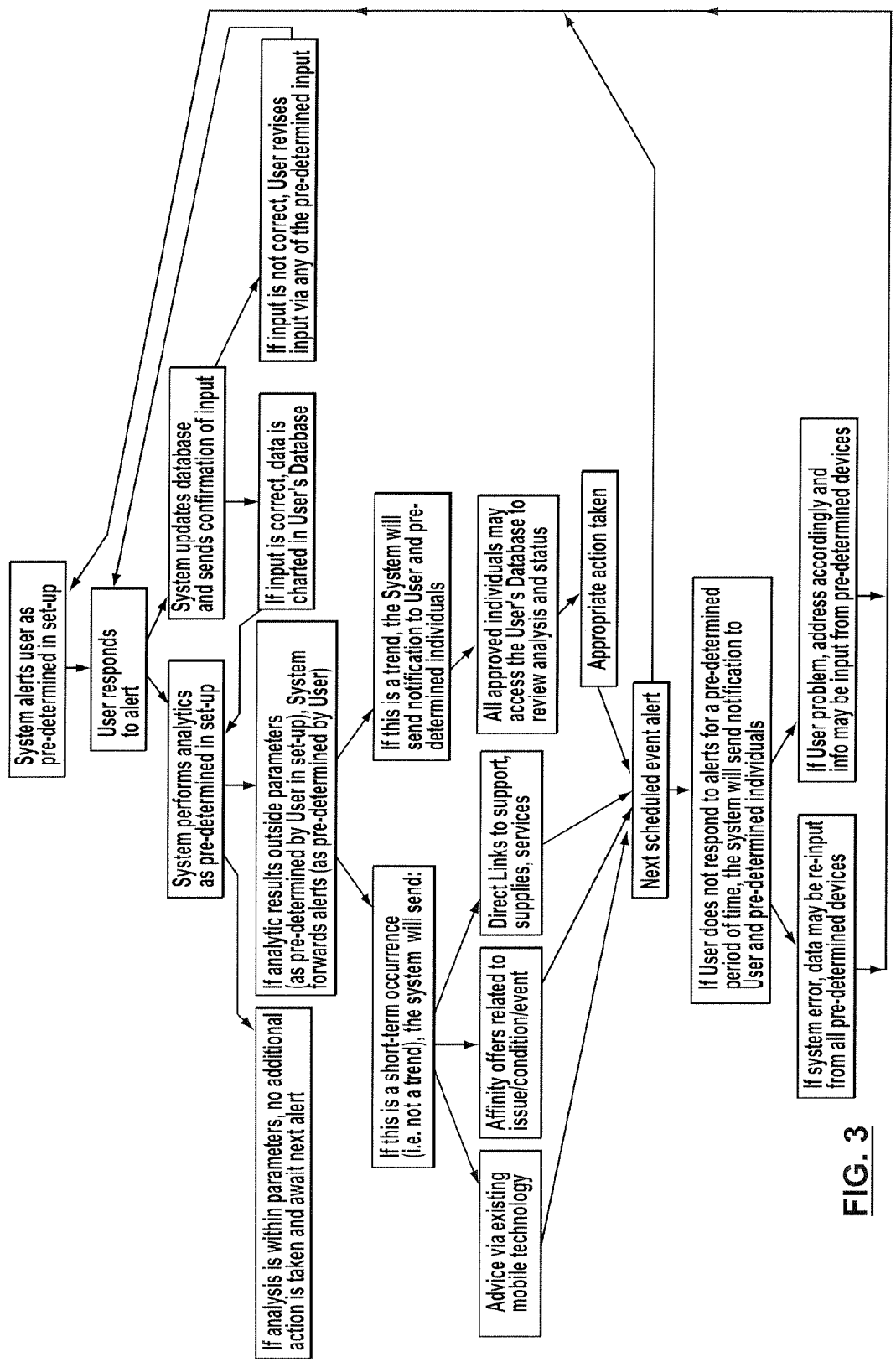
FIG. 3 is a flowchart illustrating a further aspect of the method illustrated in FIG. 2A, namely an active interface.

The user uses the input means the user provides information to the system via the active interface, an example of which is illustrated in FIG. 3. The active interface governs the relationship between the user and the system, including the responses provided by the user in response to a notification, and analysis that the system conducts.

Figure 4:
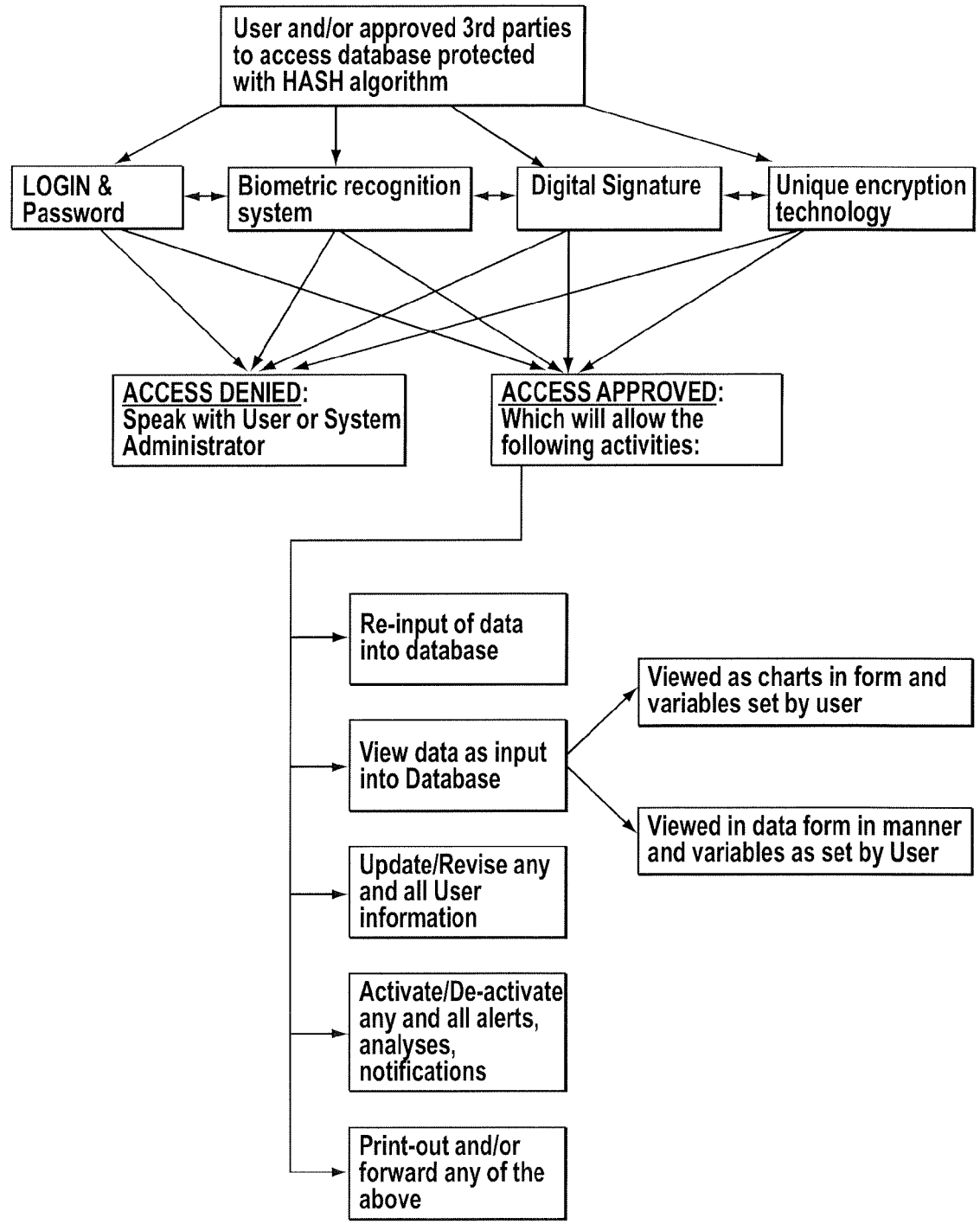
FIG. 4 is a flowchart illustrating a further aspect of the method illustrated in FIG. 2A, namely access to a database.

All information is accessible to the user and authorized third parties by accessing the database (18). As illustrated in FIG. 4, access to the database (18) is preferably protected in some way, e.g., by a HASH algorithm. This along with one or more other security techniques ensures that the information remains secure.

Once the required parameters are specified, the user submits the info for approval through the Internet (14). The administrator receives the request for approval. If the request is not approved, the administrator deletes the request and user cannot go any further. If approved, the user is sent an e-mail for confirmation. When an e-mail sent, the user is also sent phone confirmation via SMS. Once the user replies, the system notifications are set.

In a particular implementation of the present invention, once the notification scheme is established, the system provides notifications to the user. The user responds to a notification, and the system assumes that any response prior to the next notification pertains to the preceding notification. The system performs trend analysis based on parameters selected by the user. The system determines whether response is within or outside such parameters. If it is within parameters, the system sends an SMS confirmation of the specific response. If outside the parameters, the system sends a confirmation of the specific response and provides additional notification that the user is outside its parameters. The system also sends an e-mail notification to addresses as indicated and approved by the user in the application setup. These third parties (e.g., a family member or a caregiver) may access the user's database of information provided they have been given permission and the login and password information from the user.

In the event that the user does not respond for a specified period (with an example default setting being two days), the system will send an e-mail to the user notifying them of non-response and allowing them to review the account database to make required updates and/or to contact administrators/support.

In a further aspect of a particular implementation of the present invention, the user may access their database (18) via the website using their login/password and have the following options: (i) non-wireless input, namely the user has the option at any time to input information directly into database via a computer with Internet access; (ii) charted information, namely viewing of their raw data in date order (as chosen by user) or for specific date period (as chosen by user), or user may view their data on an animated bar chart in date order (as chosen by user) or for specific period (as chosen by user); (iii) the user can update or revise information, including the information at initial set-up, e.g., SMS number, password or e-mail address; (iv) the user may activate or deactivate any notifications at any time; and (v) the user may print-out the database information from the web interface.

Figure 5A:
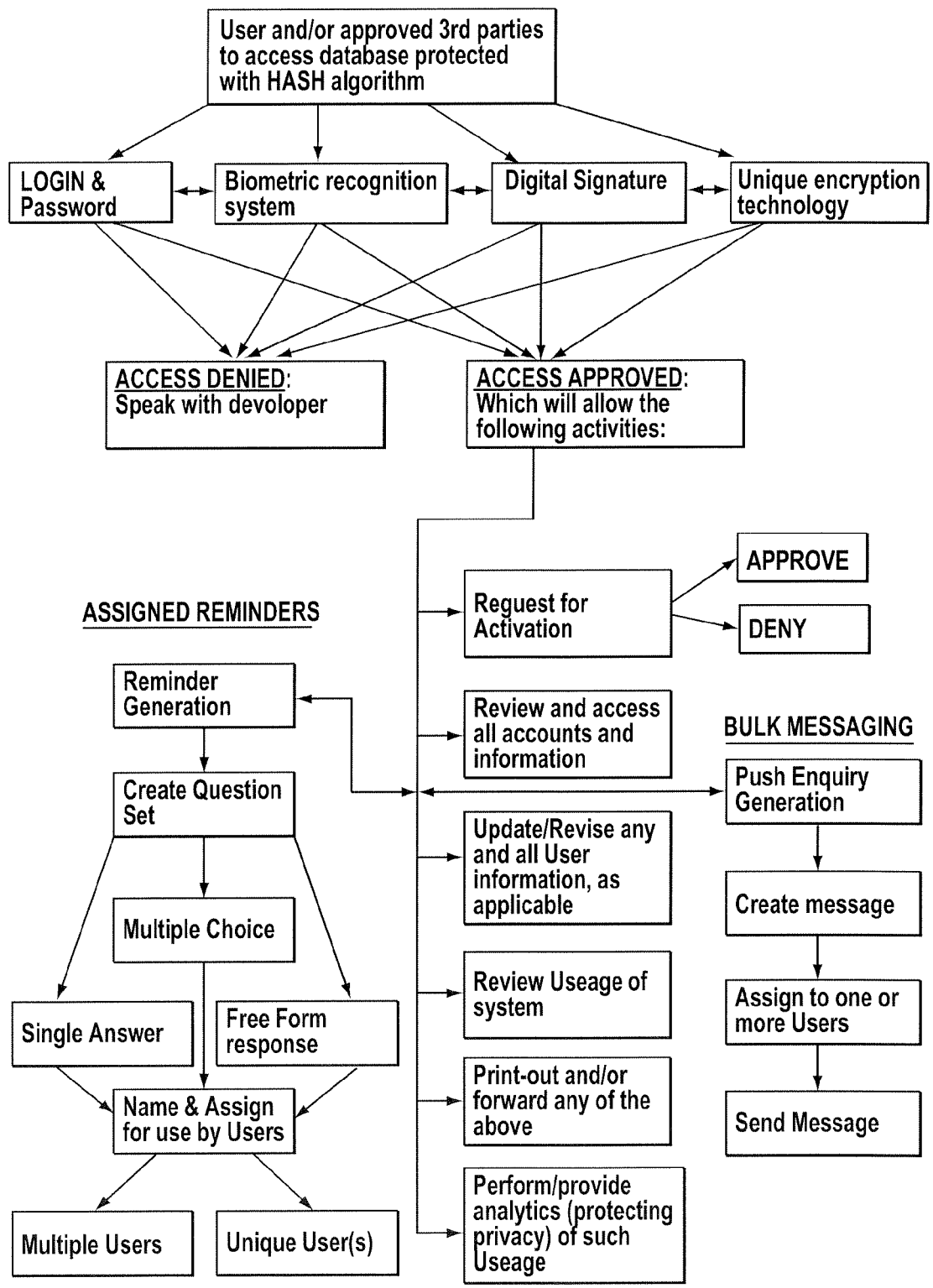
FIG. 5A is a flowchart illustrating a further aspect of the method illustrated in FIG. 2A, namely a system administrator interface.
Figure 5B:
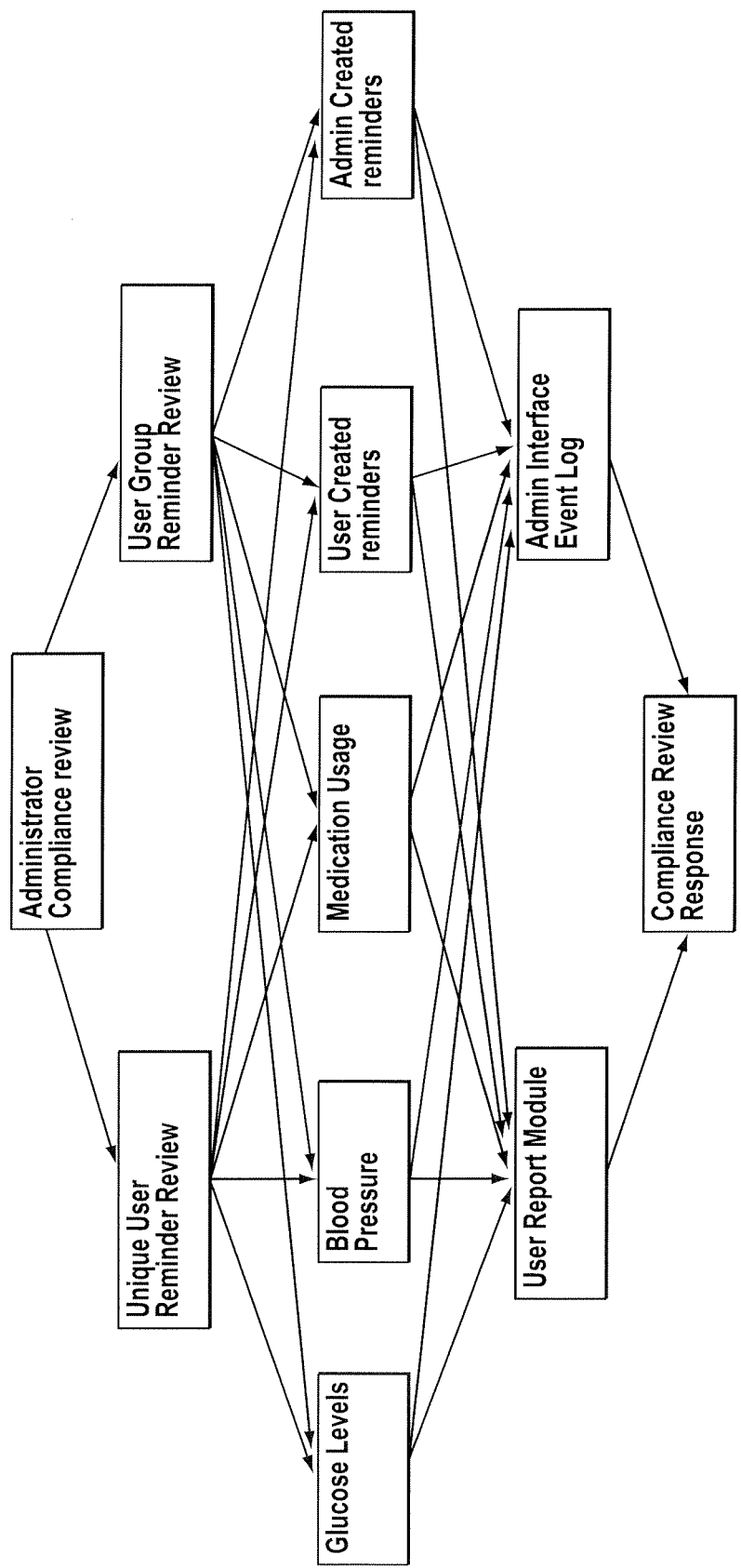
FIG. 5B is a flowchart illustrating a further aspect of the method illustrated in FIG. 2A, namely administrator user compliance review.

The administration interface of the present invention provides access to administrators to certain functions linked to the server (10). In a particular implementation of the present invention, these functions/resources are accessed via a series of web pages linked to the web server (12). The administration interface comprises a main page that prompts the user for login and password information. As an example, a flowchart illustrating a system administrator interface is provided in FIG. 5A. It should be understood that alternate means for authentication are also contemplated by the present invention. These web pages, for example, enable administrators to approve all requests for activation, review and access of all accounts (and respective databases), review usage of system via logs, etc., and provide an analysis of usage of system, accounts, etc. The administrator user compliance review is shown in FIG. 5B.

It should be understood that other functions/resources can be associated with the server (10) and made accessible via selection from possible options via user commands described in the present invention.

The present invention also provides for a plurality of notification types. In a particular implementation of the present invention, the notifications are provided by the server to the cellular phone in the form of enhanced test messaging. For example, the text notification can be a simple question, or multiple questions. In a further aspect, notifications can be multiple questions wherein each subsequent question is dependant on the previous response. The present invention also contemplates multiple notification options, including audio alerts, including musical alerts, voice alerts, and/or simple tones or ringing.

These audio notifications can be sent via MMS, and can be in mp3 or other suitable formats. A visual alert can be provided where such visual notifications are supported by the personal communication device (22). As mentioned herein, the notification can also be a direct alert linking to a third party, for example a family member or caregiver, as selected by the user. It should be understood that any notification or alert type mentioned herein can be implemented alone or in combination with other alert types, in accordance with the users' selection(s).

As mentioned, in yet a further aspect of the present invention musical notifications or alerts can be provided to the user through their personal communication device. In this regard, it is possible to correlate the particular musical piece to the various specific levels of notification or alert for the user. As an example, a notification comprising the song "Sugar, Sugar" can correspond to mild levels, whereas an notification comprising the song "No Sugar Tonight" can correspond to more serious levels. The parameter of these types of notifications can be set by the user and changed from time to time, in accordance with the present invention.

In a further aspect of the present invention, the content of notifications can comprise specific information based on database analysis. For example, the notification content can be tailored (by the user) in relation to the database analysis relevant to, e.g., dietary requirements, exercise requirements, medical condition, individual reading or measurement, and/or support requirements.

In another aspect of the present invention, the data collected by the database (18) can be linked and provided to third party systems for further processing. For example, the data can be utilized for the purpose of patient record management or processing of insurance claims, subject to privacy issues.

In one specific example of the implementation of this aspect of the present invention, the Life:WIRE system can be utilized by a pain management health provider. According to this implementation, data that is collected (by the Life:WIRE system) concerning pain levels and medication use is provided to a patient record management system to improve the data available to the patient record management system.

The specific architecture to support this example implementation can be arranged as follows. A user can be fitted with a personal monitoring device that is operable to provide pain level and medication data (e.g., using BLUETOOTH™) to a personal communication device (e.g., a BLACK-BERRY™). The personal communication device then provides this data to the Life:WIRE system, which acts as a communication broker with the pain management health provider. The pain management health provider provides for data normalization, data aggregation and secure storage, and is operable to interface with other services providers (e.g., emergency personnel, dentists, laboratory, pharmacy, etc.). Health records maintained by the pain management health provider can be directed to the particular user through their personal communication device, whether via the Life:WIRE system or directly.

In yet further aspects of the present invention, notifications can comprise yet further information and content for the user. For example, a notification can take the form of a video of a caregiver, or even of the user themselves, giving a quick lecture about the current status, corresponding to the notification level. The notification can also provide links to sites, phone numbers, and suppliers relevant to the level. Alternatively, the notification can directly provide a tie-in, via text, cell, e-mail, web, camera, etc., to the particular caregiver or support individuals, as customized by the user. The present invention contemplates each one of these possible notifications/alerts, and any combination thereof, with the type of notification and any corresponding trend analysis customizable by the user.

The information requested by each notification is dependent on the individual needs of the user. For example, for users interested in monitoring Diabetes-related attributes, the notifications will prompt the user for specific values, including, e.g., glucose levels, blood pressure data, heart rate, weight, temperature, etc. The present invention is capable of interactively monitoring a plurality of measurements.

Tailoring the content of notifications may further improve the user's success at achieving adherence/compliance to a particular health regime. In this regard, the notifications can be changed on a regular basis, and can incorporate effects or entertainment elements to make them more interesting and engaging, for example through the use of comedy.

Further, the present invention is not limited to quantitative information but is also operable to prompt the user for specific non-quantitative health or lifestyle related information related to any of the applications discussed herein. For example, the notification can consist of a simple question, such as "How do you feel?", "Do you feel alert?", and "Do you feel tired?", etc. This in turn can result in additional questions to where these qualitative questions can further yield helpful information from the user and can be correlated to other data via the data analysis aspect of the present invention. Such non-quantitative health or lifestyle related areas include dietary issues, mental health such as anxiety and exercise, to name a few.

EXAMPLE

The operation of the present invention is best understood by reference to the example below. In this particular implementation of the present invention, the Life:WIRE system is used to record glucose measurements for Diabetics. The system server notifies the patient to take his or her glucose readings from their glucometer. The patient then inputs the information and the database responds with both a confirmation of the level and notification if the levels on average are rising or falling. In the event that the level remain high or low for a determined period of time, the patient-designated individuals (caregiver, parent, physician or other) is emailed a notification to that effect.

It is to be expressly understood that monitoring of Diabetes-related conditions is only an example of the present invention in operation. The present invention comprises a plurality of applications, as detailed in the foregoing.

Figure 6:
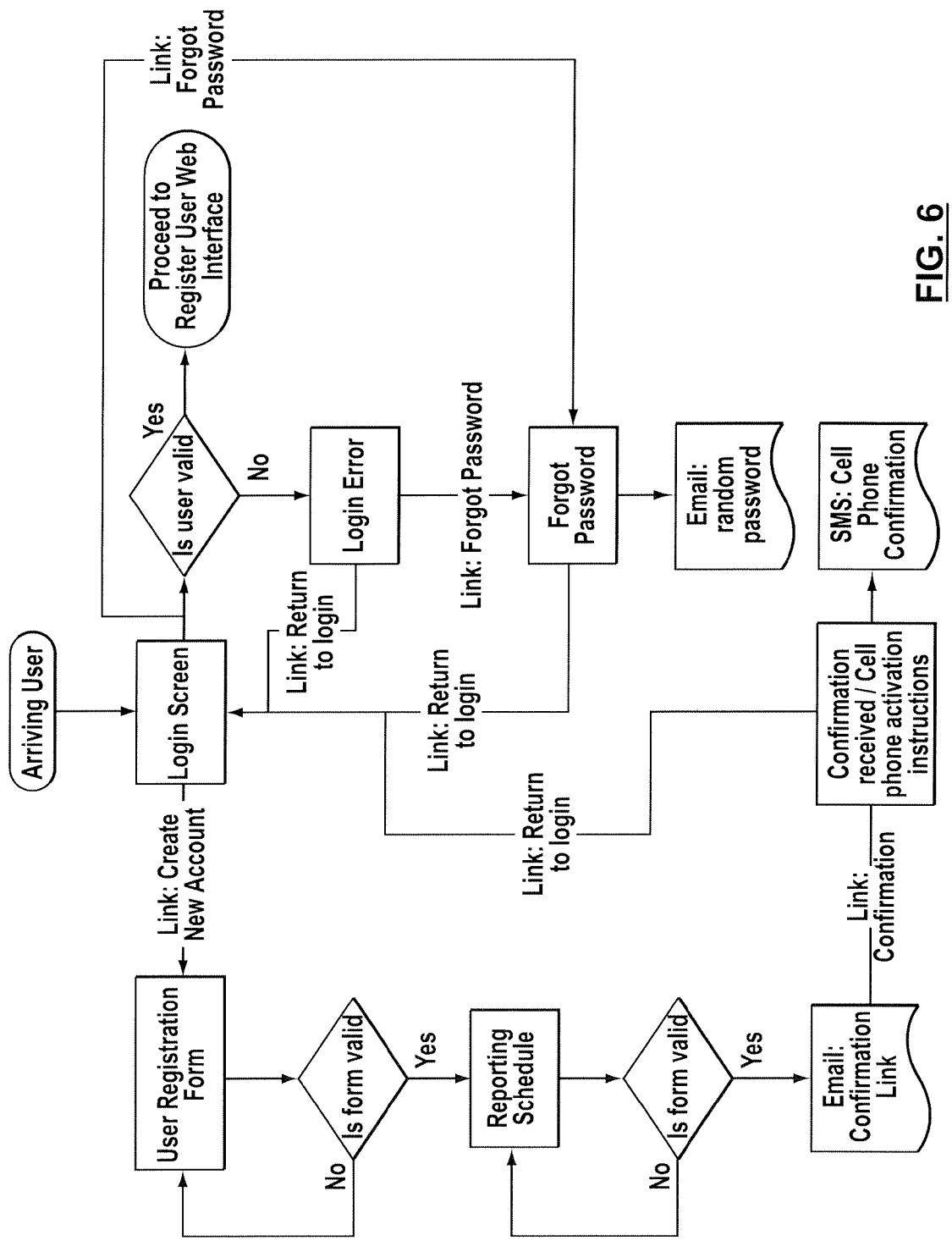
FIG. 6 is a flowchart illustrating a further aspect of one particular embodiment of the present invention, namely a user login and registration system.
Figure 7:
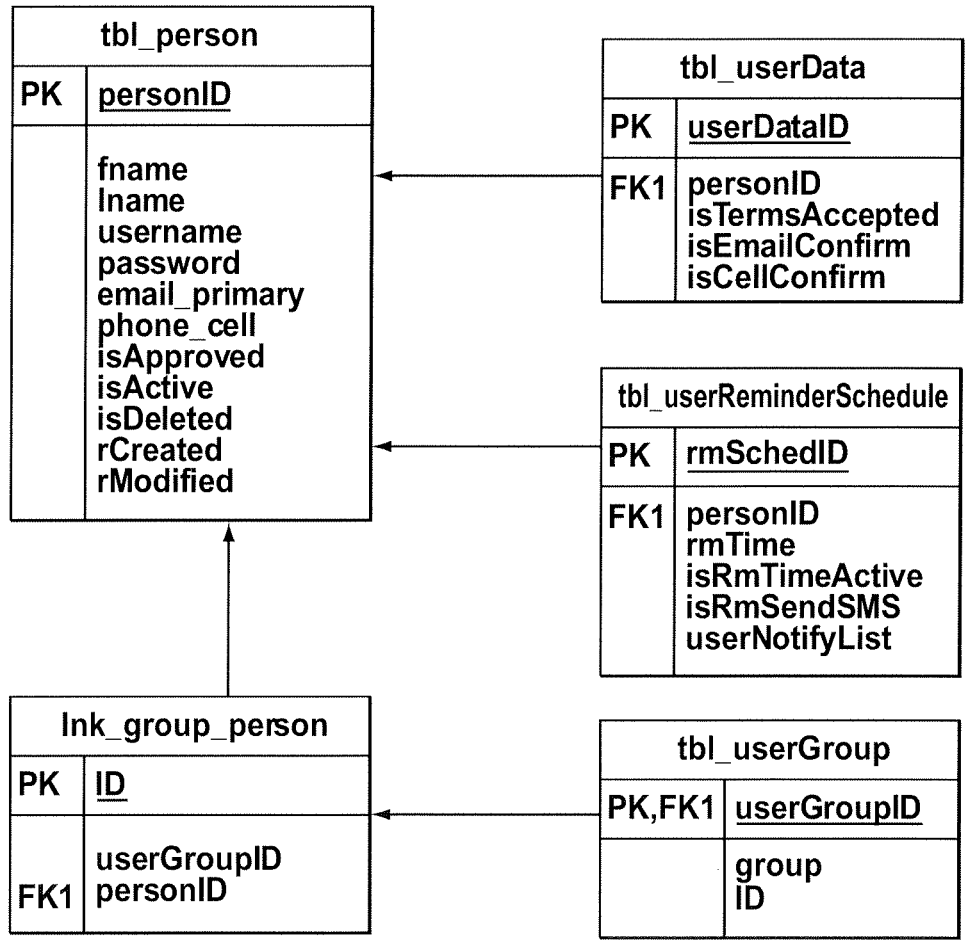
FIG. 7 is a flowchart illustrating a further aspect of one particular embodiment of the present invention, namely database schema requirements for the user login and registration system depicted in FIG. 6.
Figure 8:
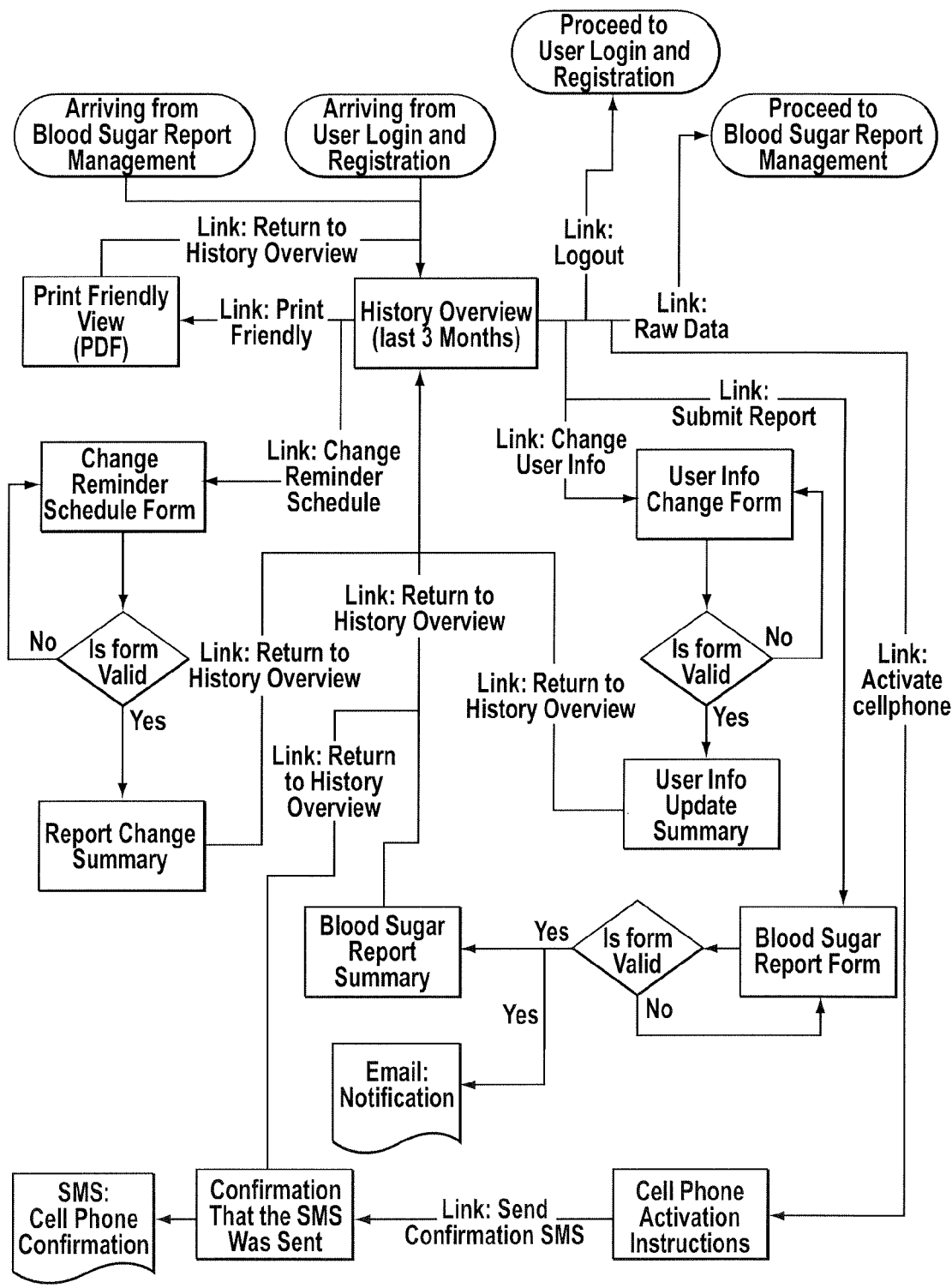
FIG. 8 is a flowchart illustrating a further aspect of one particular embodiment of the present invention, namely a registered user web interface.
Figure 9:
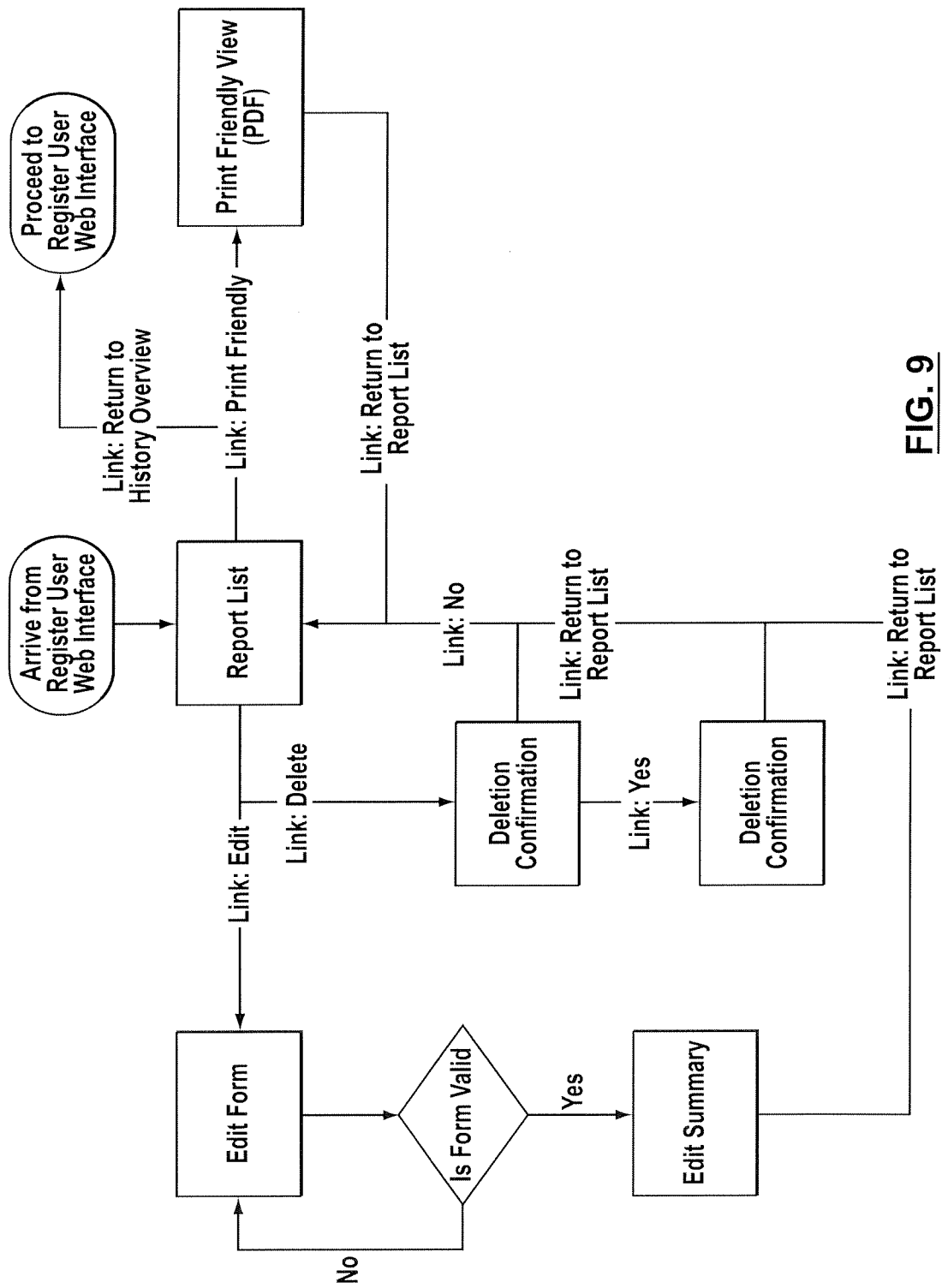
FIG. 9 is a flowchart illustrating a further aspect of one particular embodiment of the present invention, namely a blood sugar report management system.
Figures 13, 14:
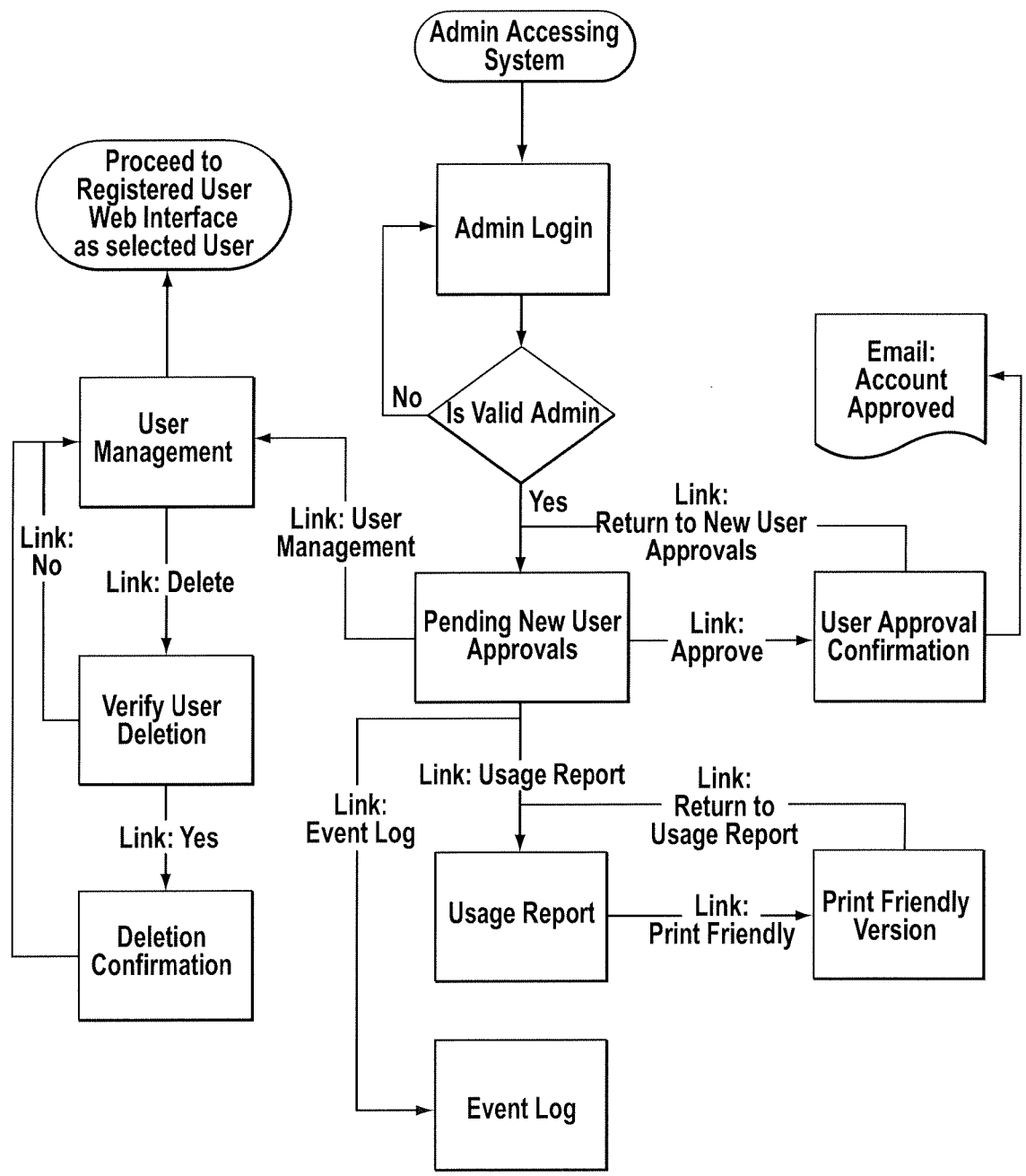
FIG. 13 is a flowchart illustrating a further aspect of one particular embodiment of the present invention, namely an administration interface.
FIG. 14 is a flowchart illustrating a further aspect of one particular embodiment of the present invention, namely database schema requirements for the administration interface depicted in FIG. 13.

More particular aspects of the example are described below and are further illustrated by reference to the Figures. Specifically: (A) FIG. 6 is a flowchart illustrating a further aspect of one particular embodiment of the present invention, namely a user login and registration system; (B) FIG. 7 is a flowchart illustrating a further aspect of one particular embodiment of the present invention, namely database schema requirements for the user login and registration system depicted in FIG. 6; (C) FIG. 8 is a flowchart illustrating a further aspect of one particular embodiment of the present invention, namely a registered user web interface; (D) FIG. 9 is a flowchart illustrating a further aspect of one particular embodiment of the present invention, namely a blood sugar report management system; (E) FIG. 10 is a flowchart illustrating a further aspect of one particular embodiment of the present invention, namely database schema requirements for the blood sugar report management system depicted in FIG. 9; (F) FIG. 11 is a flowchart illustrating a further aspect of one particular embodiment of the present invention, namely a mobile reporting system; (G) FIG. 12 is a flowchart illustrating a further aspect of one particular embodiment of the present invention, namely database schema requirements for the mobile reporting system depicted in FIG. 11; (H) FIG. 13 is a flowchart illustrating a further aspect of one particular embodiment of the present invention, namely an administration interface; and (I) FIG. 14 is a flowchart illustrating a further aspect of one particular embodiment of the present invention, namely database schema requirements for the administration interface depicted in FIG. 13.

1. User Login and Registration System

In an embodiment of the present invention, every new and registered user accessing the Life:WIRE system will require a username (which can be an e-mail address) and password. This system is illustrated in FIG. 6; the database schema requirements for this are illustrated in FIG. 7.

(a) Login Screen

In one particular implementation of the present invention, the login screen will be the default page seen by any user attempting to access the site that is not logged in. The page will allow the user to enter their username (e-mail address) and password and then click a login button to confirm that their credentials are valid. Should the user information provided prove valid, the user will proceed to the "History Overview" page which is covered under the "Registered User Web Interface". Should the credentials the user supplied be invalid, the user will be sent to the "Login Error" page that is detailed below.

This login screen will also include a link labelled "Forgot Password?". This link will lead to a webpage that will allow a user to receive a new password via e-mail.

There will also be a link labelled "Create New Account". When a new user arrives at the site they would use this like to begin the account creation process.

Users will be assigned to specific roles within the system. These roles include administrators, alpha testers, beta testers and general users. The user roles are set in the tbl_userGroup table and can be adjusted as needed. The roles control what functionality the users have access to within the system.

(b) Login Error

Should the user's credentials be invalid, they will be directed to this page. They will be notified that there has been a problem with the information they supplied and provided options to proceed.

The user will be able to use a link to return to the "Login Screen". There will also be a link to the "Forgot Password?" system.

Finally, there will be the option to "Create a new account" that will link the user to the "User Registration Form".

(c) User Registration Form

In this embodiment of the present invention, the user registration form is the first step in creating a new account. The user must provide his/her first and last name, a valid e-mail address that will also act as their username, the cell number they wish use, and a password. The password field will be masked so users will be required to enter it twice to ensure that they do not make a mistake. Once the user has completed the registration form they will click the "Next" button to continue to the "Reminder Schedule" page. During the submission process, the data that the user entered will be verified and, should a field have been left blank or was filled-in incorrectly, the browser will return to the "User Registration Form" with the errors highlighted at the top of the page.

(d) Reporting Schedule

Once a user has completed the "User Registration Form", they will be asked to fill in the "Reporting Schedule". The user will be presented with the option to input as many notifications, which in this case are reminders, as they choose and at which time they would like to have the reminder sent. They will also have the option to determine the nature of the reminders such as requiring the input of glucose levels or confirmation of having taken medication. The user will be able to change these times, and nature of reminders and they will also have the ability to turn any or all of the reminders off. They will also have the option of setting a reporting time but not having that time send out an SMS reminder.

Under the reminder time area will be three blank text boxes where the user can enter in e-mail addresses. These three e-mail addresses will be copied on any notifications that are sent the user's cell phone. The e-mail fields can be left blank.

In addition, the user will set their personal settings which allows the user to create the parameters under which the invention analyses the respective data trends. For example, in the measurement of glucose levels, it will allow for the user to determine the upper and lower limits and the number of measurements to use for such analysis. If the data trends go above or below such parameters, the invention will send a notification of that event to the pre-determined above When the user has completed the form, they will click on the next button to continue. The page will check the times to make sure that they do not overlap.

Once the process has been completed, the page will display a thank you message and a note stating that a confirmation e-mail has been sent. The confirmation e-mail will contain a link that will have to be clicked on to verify the validity of the account. More information on the e-mail can be found below.

The scheduled reminders will be stored in the tbl_userRemindersSchedule table, as illustrated in FIG. 7. This table is designed to be scalable so that the number of reminders is scalable as the system is further developed. For this example, users will be limited to and prompted to use up to six reminders, however this is a soft requirement based on the forms and not the data structure.

(e) E-mail: Confirmation Link

Once the user has completed the various web forms that are required to create an account they will receive an e-mail. This e-mail contains a link that returns the user to the website and confirms that the e-mail account that is associated with the new account is in fact accessible to the user. The link will send the user to the "Confirmation Received/Cell Phone Activation Instructions".

(f) Confirmation Received/Cell Phone Activation Instructions

When a user clicks on the link supplied to them in the "E-mail: Confirmation Link", they will be sent to this page. The page will confirm that the user's web account will be activated once an administrator approves the account. The page will also inform the user that a SMS message has been sent to their cell phone. "SMS: Cell Phone Confirmation" section has more information on the details of the message. This page will also contain a link back to the "Login Screen" and the text for that link should read "Back to User Login".

(g) Forgot Password

Should a user have forgotten their password, they will be able to use the "Forgot Password" page to retrieve it. The user will be asked to enter the e-mail address they used to create their account and then hit a "Send Password" button. The page will then create a random password for the user's account and send that password to the user in an e-mail. More information on the e-mail can be found under the heading "E-mail: Random Password". Should the e-mail address entered not be registered with the Life:WIRE system, the page will inform the user that the e-mail is not recognized.

(h) E-mail: Random Password

Should the user forget their password, they can request that the site create a new one and e-mail it to them. They will then receive an email that contains a new randomly generated password.

2. Registered User Web Interface

According to a particular implementation of the present invention, when a user wishes to review their blood sugar report history or make changes to their user account information, they will be able to do so via the "Registered User Web Interface". This interface is illustrated in FIG. 8. A user will need to have an account registered with the system and be logged in.

(a) Navigation System

A universal navigation system will be present on every page that is part of the web-based interface that a user interacts with while logged in. The navigation system will include links to the following locations: "History Overview"; "Blood Sugar Report Form"; "Blood Sugar Report Management"; "Change Reporting Schedule"; "Change User Information"; "Cell Phone Activation" (only appears if cell not active); and "Logout".

(b) History Overview

When the user logs into the web site, they have the option to come to this page. The page is meant to summarize the most recent data based on the user's reporting. The user will be presented with a bar chart of their average blood sugar level on a weekly basis. They will also see a graph of their reporting history displayed with each row containing a full day of reports.

The user will be able to adjust both the total time frame of the blood sugar chart displays (1 month, 2 months, 3 months, etc.) as well as the time each bar represents (daily, weekly etc.). Should a user's account not contain enough data to fill the requested time frame, the bars that do not have data will be set to zero.

The graph of reported data will adjust to the number of reporting times the user has set-up. For example, if the user has opted to only report their blood sugar 3 times per day, each day will only show 3 reports. The chart will display reports from newest to oldest. The user will also have the option to view a print-friendly version of this page that they can take with them to their 3-month check up.

(c) Print-Friendly View (History Overview)

Should a user wish to print a version of the "History Overview", they will click on the "Print-Friendly" link on that page. They will be presented with a page containing only the historical data (both chart and graph) that is formatted to fit within the margins of a standard 8"×11" sheet. There will be a link on this page that will return the user to the "History Overview".

(d) Change Reporting Schedule Form

Through the use of the Life:WIRE system a user may decide that their original reporting schedule is not working. They will be able to use the "Change Reporting Schedule Form" to make changes to these settings. The page will work very much like the "Reporting Schedule", barring a few exceptions. The first is that rather than a blank form appearing, the page will automatically fill in all fields with the current user's information. The second variation is that once the user has submitted the form they will be sent to the "Reporting Change Summary". The form will be verified against the same criteria as the "Reporting Schedule".

(e) Reporting Change Summary

Once the user has submitted the changes they would like to see to their reporting schedule they will be sent to this page. The page will contain a summary of their new information and verification that the changes have been made. A link at the end of the summary will lead the user back the "History Overview" page.

(f) User Info Change Form

If the user needs to make a change to their account information they will be able to do so via this form. This form is very much like the "User Registration Form" with a few exceptions, namely the form will be filled-in with the current user's account information when it load, and the user will not be able to change their e-mail address. Once the user has completed the form and the data has been verified as properly entered the user will be sent to the "User Info Update Summary".

(g) User Info Update Summary

Once a user has updated their user information they will be sent to this page. The page will display their updated user information and confirm that the database has been changed. Should the user have changed the cell number that is associated with their account, the summary page will send out a "SMS: Cell Phone Confirmation" message, as the new number will need to be confirmed before it is used. The page will also have a link back to the "History Overview" page.

(h) User Info Update Summary

Once a user has updated their user information they will be sent to this page. The page will display their updated user information and confirm that the database has been changed. Should the user have changed the cell number that is associated with their account the summary page will send out a "SMS: Cell Phone Confirmation" message, as the new number will need to be confirmed before it is used. The page will also have a link back to the "History Overview" page.

(i) Blood Sugar Report Summary

Once an online blood sugar report is successfully entered into the system, the user will be sent to this page where they will see a confirmation of their submission and be presented with a link back to the "Historical Overview". Should the user's average blood sugar be outside of the recommended range over the past 10 reports, the system will show a warning message on this page and send out an "Email: Notification" to requested recipients. This will occur unless the report entered is more than one day old.

(j) Cell Phone Activation Instructions

Should the user have ignored or deleted the original "SMS: Cell Phone Confirmation" that was sent to them during the account creation process, they will be able to use this system to confirm their cell phone number at anytime. This page will give the user instructions on the confirmation process followed by a link to the "Confirmation that the SMS was sent" page.

(k) Confirmation that the SMS was Sent

The user will be notified that an SMS message has been sent to their cell number and that they should reply to it in order to confirm their cell number. The user will then follow a link at the bottom of the page back to the "History Overview" page. The rest of the process is covered under the "Mobile Reporting" section of this document.

3. Blood Sugar Report Management System

In a further aspect of the particular implementation of the present invention, a user may want or be required to change or delete blood sugar reports. This may be due to errors made during the reporting process. The "Blood Sugar Report Management System" is an interface that will allow user to manage their blood sugar reports. This system is illustrated in FIG. 9; the database schema requirements are illustrated in FIG. 10.

(a) Report List

This page will show a list of reports. The reports will be in the form of a table and the user will have several options to alter the view. Each record will have links associated with them that will allow the user to either edit or delete the record.

Due to the potential number of records that could be displayed, the page will only show 20 records at a time. The user will be allowed to scroll through the reports 20 records at a time.

The user will also be able to refine the number of records shown by restricting the time frame. The user will be able to set a start date and end date and any records that where entered during the specified period will be displayed.

The reports will be displayed in a chart. "Edit" and "Delete" found in the command column will be links to the "Edit Form" and "Deletion Confirmation" pages, respectively. They will allow the user to perform either operation on the specific report with which they are associated. The page will also have a link to the "Print-Friendly View (Report List)" page.

(b) Print-Friendly View (Report List)

Should a user wish to print out a version of the "Report List", they will click on the "Print-Friendly" link on that page. They will be presented with a page only containing all the reports in the selected time frame formatted to fit within the margins of a standard 8"×11" sheet. There will be a link on this page that will return the user to the "Report List" page.

(c) Edit Form

The user can select to edit a blood sugar report from the "Report List", which will lead them to this page. The user will be able to change the date, time, and blood sugar level associated with the record. Once the user has made the necessary adjustments they can submit their changes, at which point any error will be reported. If the record is acceptable the user will be sent to the "Edit Summary" page. Any alteration will not trigger a warning to be sent out.

(d) Edit Summary

Once a blood sugar record has been updated the user will be shown a summary of the changes they have made on this page. The user will then be presented with a link back to the "Report List" page.

(e) Deletion Confirmation

Should a user select to delete a record from the "Record List", they will be sent to this page. They will be asked to confirm the deletion request. If they click on 'Yes' the user will be sent to the "Deletion Confirmed" page. If they select 'No' the user will return to the "Report List" page.

(f) Deletion Confirmed

The user will be sent to this page once they have confirmed that they would like to delete a specific record. The page will confirm that the record has in fact been removed from the database. The user will then be able to take a link back to the "Report List".

4. Mobile Reporting

According to an embodiment of the present invention, most of the day-to-day interaction with the Life:WIRE system will be conducted via the cell phone rather than on the web.

One aspect of this mobile reporting is the reporting window. Should a user register six reporting times in one day, they have created six windows during which time they must submit their reports. For example, a user has set their first reporting time to start at 9 am and the next to start at 12 pm. Any message sent in between these two times will be considered a valid first window report and will show up on their report chart under the heading 1. Should the system receive two reports during one of these windows, only the first report will be considered valid.

An issue facing the mobile portion of the Life:WIRE system is what to do when a user leaves a cell area or turns off their cell for long periods of time. The SMS system will be required to identify that a user is not receiving messages and stop sending in order to avoid messages piling up and reduce any sending cost that may be incurred. The server will need to be able to recognize when the user has reconnected and resume sending messages at that point.

The mobile reporting system is illustrated in FIG. 11; the database schema requirements are illustrated in FIG. 12.

(a) SMS: Cell Phone Confirmation

At various times a user will need to confirm that they have access to the cell phone number they have provided. The confirmation process will start with this message being received by the user's cell phone. The message will instruct the user to simply reply to the message with the letter "Y" to confirm that they wish their cell phone to receive messages from the Life:WIRE system.

(b) SMS: Phone Verification Received

Once a user replies to the "SMS: Cell Phone Confirmation" and the server has successfully received their confirmation message, the user will be sent a follow-up message informing the user that their phone will now receive reminders.

(c) SMS: Reminder Received by User

The server will send out a reminder to the user's cell phone at specified times requested by the user. This message will inform the user that they should check their glucose levels and reply to the message with the result. The user should then reply to the message to report their blood sugar level. Any report the user sends back prior to the next reporting window commencing will be considered a successful response to this message.

(d) SMS: New SMS Report Sent to Life: WIRE Number

In some instances a user may request not to be sent a reminder yet still wish to report their blood sugar. They would be able to do so by sending a message to the Life:WIRE number and reporting their glucose level.

(e) Enter Glucose Level

The user will be required to enter in their blood sugar level as reported by their glucometer into a text message and send it to the Life:WIRE SMS number. This process will require the user to be able to enter in numbers and decimal places via their cell phone.

When a user enters their blood sugar, the system will assume that they are entering in a number with at least one decimal place. Should the user enter a decimal point into their blood sugar level they submit, the system will accept the message as it is sent. Should the user not put in a decimal point, the system will assume that the last digit is after the decimal place. For example, 112 would be converted to 11.2.

(f) SMS: Confirm Receipt of Report

The server will send the user a confirmation that their blood sugar report was received and display how their report was interpreted by the system. This message will only be sent out if the user's blood sugar level does not trigger a warning.

(g) SMS: Send Warning to User

If a user's average blood sugar is outside of recommended bounds over the last 10 reports, the user will be sent a warning message that displays their current average blood sugar level and inform them that it is to high or low and that the user should take action in order to correct the variance. In addition, should a user's blood sugar have been well maintained during this period, a message will be sent stating that they have stayed within their desired range on average over the last ten reports.

(h) E-mail: Send Warning to Alternative Contacts

Should a user's report indicate that their average blood sugar level over the last 10 reports is out of the recommended range, all the alternative e-mail addresses registered to their account will receive and e-mail copy of the warning.

5. Administration Interface

According to an embodiment of the present invention, Life:WIRE administrators will require an interface that will allow them to perform administrative tasks on the system and view usage statistics. This portion of the system will not be accessible to the public and will require an administrator (admin) to login with a special username and password.

The administration interface is illustrated in FIG. 13; the database schema requirements are illustrated in FIG. 14.

(a) Admin Login

An administrator (or "admin") wishing to access the administration interface will go to a special web address that will bring them to the administrator login screen; at which point they will be required to enter in a username and password. Should the administrator enter in a valid username and password they will proceed to the "Pending New User Approvals" page. Should the login criteria the user supplied prove invalid, they will return to the login screen which will display an error message.

(b) Admin Navigation System

An admin navigation system will be present on every page that is part of the admin interface and that is accessible while logged in. The navigation system will include links to the following locations: "Pending New User Approvals"; "User Management"; "Usage Report"; "Event Log"; and "Logout".

(c) Pending New User Approvals

Once an administrator has successfully logged in, they will be presented with a list of new user accounts that are awaiting approval. The list will only show accounts that have never been approved before.

User information is listed in a chart. The first field will show the user's name, the second will show their email address. A field marked "E-mail Conf" will show weather the user has confirmed their e-mail address with the system. Similarly, the "Cell Conf" field shows whether the user has successfully registered their cell with the system. The last column contains a link called "Approve" should an admin click on the approve button the users account will be activated and the admin will be sent to the "User Approval Confirmation" page. The admin will also have the option to delete the new account which will send the admin to the "Verify User Deletion" page.

(d) User Approval Confirmation

Once an admin has approved a new user, the admin will arrive at this page where they will see a notice that the user has been successfully approved and that the "E-mail: Account Approved" has been sent to the user notifying them of the activation of their account. The page will include a link back to the "Pending New User Approvals" page.

(e) E-mail: Account Approved

Once an admin has approved a user's account, the system sends the user a copy of this e-mail. They will be notified that they may now log into the system.

(f) User Management

Throughout the course of the normal operation of the Life:WIRE system, admins may be required to aid users with system problems or perhaps delete accounts that are no longer in use. The "User Management" page will allow the admin to view all the current approved accounts in the system. The chart therein is very similar to the one described under the "Pending New User Approvals" section, however, it has one key difference. Under the command column, there is a link labelled "Login". Should the admin wish to investigate issues with a particular user's account, they can click this link to login as that user. This function is important as it allows an admin to help a user without the user having to reveal their password to the admin.

As the list of users may grow quite long, each page will only show 20 records at a time and the admin will be able to page through them 20 records at a time. They will also have the option of entering in part or a user's entire name to search for a specific account. Any accounts that mach the criteria will be displayed so that partial names can be entered.

(g) Verify User Deletion

Should an admin decide that it is necessary to delete an account from the Life:WIRE system, they will arrive at this page where they will be asked to confirm the decision. They will be presented with two links, the first will be labelled "Yes" which will send them to the "Deletion Confirmation" page. The link will return them back to the "User Management" page or the "Pending New User Approvals" page depending on where they initially clicked the delete link.

(h) Deletion Confirmation

Once an admin has confirmed that they do, in fact, wish to delete an account, they will see this page that will confirm that the user account has been deleted and provided them with a link back the either the "User Management" page or the "Pending New User Approvals" page depending on the status of the record that was deleted. A deleted account will not actually be purged from the database but rather flagged as deleted and ignored by the system. This is important for potential data recovery.

(i) Usage Report

As the main goal of this system is to prove its own validity, the usage statistics will be a very important part of the admin interface. The usage report will display the following statistics: "Total Number of Approved Accounts"; "Total Number of Approved Accounts with Activated Cell Phones"; "Total Number of SMS Messages Sent"; "Total Number of SMS Messages Received"; "Average Number of Reminders Responded To"; "Average Number of Reminders Ignored";

"Average Number of Report Windows Filled"; "Average Number of Report Windows Empty"; "Average Blood Sugar Level 3 Months Ago"; "Average Blood Sugar Level 2 Months Ago"; "Average Blood Sugar Level 1 Month Ago"; "Total Number of Users that Report 80-100% As Expected"; "Total Number of Users that Report 60-80% As Expected"; "Total Number of Users that Report 40-60% As Expected"; "Total Number of Users that Report 0-40% As Expected"; "Average Blood Sugar Level of Users with 80-100% Reporting"; "Average Blood Sugar Level of Users with 60-80% Reporting"; "Average Blood Sugar Level of Users with 40-60% Reporting"; and "Average Blood Sugar Level of Users with 0-40% Reporting".

An admin will also be able to produce a print-friendly version of the usage reports by clicking on the "Print-Friendly" Link.

(j) Print-Friendly Version (Usage Report)

Should a user wish to print a version of the "Usage Report" they will click on the "Print-Friendly" link on that page. They will be presented with a page containing only the usage statistics that are formatted to fit within the margins of a standard 8"×11" sheet. There will be a link on this page that will return the user to the Usage Report.

(k) Event Log

The event log is a simple chart of all the events that have occurred through the invention. The chart will have to fields: "Event Type" and "Message". There are four types of events that can occur: "User", "Admin", "System", and "Error". An admin will be able to view these logs 50 events at a time and will have the option to scroll through them. They will also be able to select a time frame to reduce the total number of records shown. The exact messages that will accompany each event will be determined during the production of the system. It is through the "Event Log" that administrators can monitor compliance of any element of the invention. The "Event Log" displays all activities such as time that an reminder was triggered, to which user it relates (which has a unique identifier), when a reminder was sent (which has a unique identifier relating to each unique user), when a response was received and what response was provided by the user.

Business Model

In yet another aspect of the present invention, a business model is proposed wherein revenue is generated from services fees. In this regard, Life:WIRE is a hosted service where hospital groups, private clinics and corporations can purchase subscriptions for their patients and employees in order to enhance their health care service or improve the effectiveness of their health plans. A white label hosted solution will give public health care services, insurance companies, HMO's, public sector insurers, pharmaceutical companies and medical measurement devices firms a branded application to complement their other health management initiatives and raise awareness and reduce customer switching for their products. A branded installed solution for telcos can increase SMS revenues, add a subscription service to their offering and convert cell phone to an affinity medical device, thereby reducing customer churn. Additionally, companies currently offering PC-based disease management solutions can add a branded mobile interface to their application utilizing the present invention. These companies can begin generating recurring revenue for the service rather than one-time software licensing fees. For example and without limiting the foregoing, the service providers can opt to charge users on a fee per use basis (e.g., $0.10 per message), or, alternatively, on a monthly fee per user basis (e.g., $7.95 per month) which provides for a set number of messages (e.g., 100) and then a set charge for any message exceeding that amount.

Figure 15:
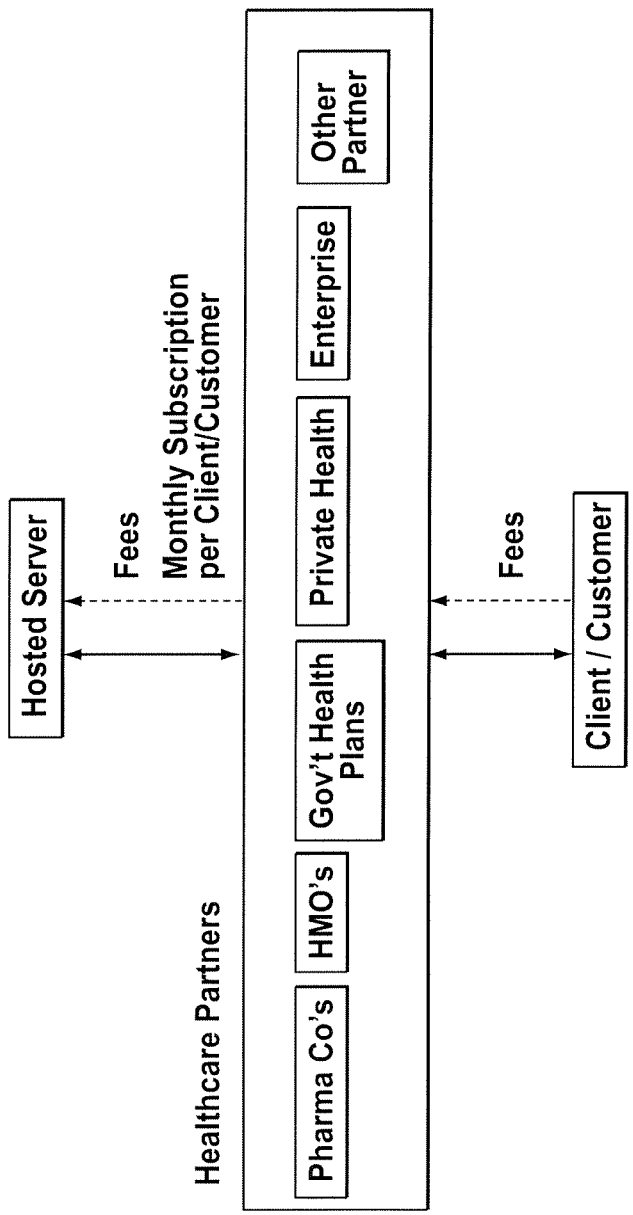
FIG. 15 is a flowchart illustrating an embodiment of a method of generating revenue in accordance with the present invention.
Figure 17:
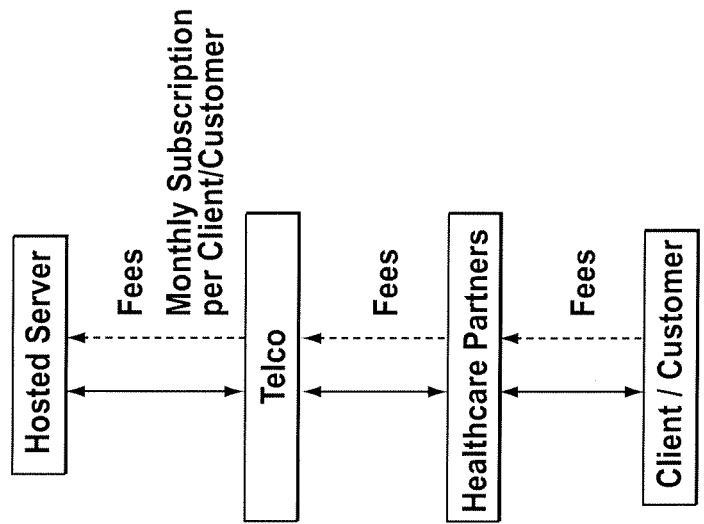
FIG. 17 is a flowchart illustrating a further embodiment of a method of generating revenue in accordance with the present invention.
Figure 16:
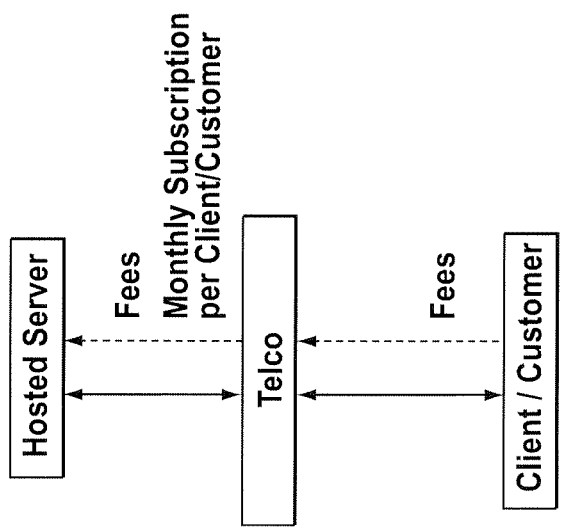
FIG. 16 is a flowchart illustrating another embodiment of a method of generating revenue in accordance with the present invention.

An embodiment for the revenue generation method of the present invention is provided in FIG. 15. In this embodiment, the healthcare service providers, including pharmaceutical companies, HMO's, governmental and private health plans, or others directly provide the Life:WIRE service to their client base, charging a monthly fee. This is advantageous because the service is provided to an already existing customer base. Alternatively, the fees and the service can be controlled through the telco, as illustrated in FIG. 16. In a further alternative embodiment, the revenue generation method comprises the telco and the healthcare partners working together to provide the service and collect fees (as shown in FIG. 17).

It should be understood that this revenue generation means contemplates the creation of relationships with sponsors of the service, such as, for example, an insurance company or other commercial sponsor. The relationship created with the sponsors may include certain "incentives" provided to the end users, including, for example, on a per notification basis. For example, for each notification a retail sponsor might provide a cash incentive or an incentive by allocating a certain number of loyalty points to the end user. Retail operations, for example, now market branded wireless services. The present invention, in one particular aspect thereof, provides a way in which to add value to the wireless services provided, and to cross-sell other products or services. For example, a response to a notification carried on a retail company's wireless service would result in allocation of a predetermined number of loyalty points redeemable for groceries sold by the retail company.

In particular, such incentives or rewards could come from the healthcare providers/client with whom the user is involved and entails passing on a portion of the savings realized on long term proper management. For example, as the estimated actuarial healthcare cost for an individual is reduced through the use of Life:WIRE, an insurer may offer a reduced insurance rate (e.g., if the insurer has a reduction of 40%, as per ADA studies, they may pass on 15% of such savings for those clients using Life:WIRE). Another example may be with the volume of use of Life:WIRE a telco may offer volume reductions in service charges or provide free minutes.

In general, the types of such incentives can be categorized as follows:
 free estimates, samples or analyses;
 products or services for no extra cost;
 product or service discounts;
 product or service time extensions;
 phone free extra minutes or services;
 extended or life memberships;
 exclusive or charter memberships;
 group discounts;
 extended warranties;
 draws for prizes;
 free music, video or movie downloads; and/or
 reduced costs or free service on peripheral items or services.

What all this does for the revenue generation side is to increase use and compliance by users through these incentives and rewards, which in turn keeps their satisfaction and use high, meaning they remain subscribed on the service. With such use and compliance, the client (e.g., an HMO) realizes the benefit of reduction in costs of healthcare management thus encouraging them to direct more of their patients to use Life:WIRE.

What is claimed is:

1. A computerized method of monitoring patient health using a patient-managed monitoring scheme, the method being performed by a server configured to manage a patient account associated with a patient and an administrator account associated with an administrator of the patient, the method comprising:
   providing a patient interface configured to authenticate a patient and enable communication between the patient and the server during a patient-authenticated session on the patient account;
   providing an administration interface configured to authenticate an administrator and enable communication between the administrator and the server during an administrator-authenticated session on the administrator account;
   receiving, from a device associated with the patient account, a proposed monitoring scheme including settings for notifications and monitoring parameters manually selected during the patient-authenticated session on the patient account;
   providing, by the server, an indication of the proposed monitoring scheme to a device associated with the administrator account;
   receiving approval information from the device associated with the administrator account, the approval information including an approval indication of the proposed monitoring scheme input during the administrator-authenticated session on the administrator account;
   based on the approval information, updating a database entry associated with the patient account and activating the proposed monitoring scheme;
   generating instructions for monitoring quantitative and qualitative data based on the settings for notifications and monitoring parameters, wherein the settings for notifications and monitoring parameters include:
      one or more messages chosen or manually-created during the patient-authenticated session, the one or more messages including personalized queries for lifestyle attributes,
      one or more alert and reminder threshold settings for alerts and reminders defined to be sent in relation to at least one of response data associated with a query sent to the device associated with the patient account, a schedule, or specific events, and
      one or more schedules for providing the personalized queries to the patient;
   sending at least one query to the device associated with the patient account, based on the personalized queries chosen or manually created during the patient-authenticated session;
   one of:
      receiving response data from the device associated with the patient account, or
      generating response data indicating a lack of a response from the device associated with the patient;
   analyzing the response data based on the one or more alert and reminder threshold settings;
   choosing at least one alert or reminder from the settings, based on at least one of the one or more schedules or the analysis of the received response data; and
   transmitting the chosen alert or reminder to at least one of the device associated with the patient account or one or more other devices associated with one or more other third parties.

2. The method of claim 1, wherein the device associated with the patient comprises at least one of the following: a personal computer; a cellular phone; one or more health sensors for temperature, blood pressure measurement, or heart rate; a smart phone; a short-range wireless device; or a cellular phone having one or more health sensors embedded therein.

3. The method of claim 1, comprising the further steps of:
   receiving, from the patient, a request to modify the one or more notifications to:
      monitor at least one of the one or more attributes relevant to a health or lifestyle condition of the registered patient;
      track medication ingested by or administered to the registered patient;
      choose the number of notifications;
      schedule the notifications; or
      require information to be transferred to any of the one or more other persons that may be a family member or a healthcare provider.

4. The method of claim 1, further comprising collecting the response data from one or more of:
   a glucometer; a heart rate monitor; a blood pressure monitor; a distance monitor;
   a global positioning system; or any other lifestyle or health attribute monitor.

5. The method of claim 1, further comprising confirming the response data by a confirmation means for providing said confirmation before analyzing the response data.

6. The method of claim 1, further comprising:
   (a) receiving a request from a patient to choose or create the one or more queries to include content relating to a lifestyle protocol including data parameters prescribing a range of acceptable response data values for the lifestyle attribute relating to said query; and
   (b) receiving a request from a patient to choose or create the one or more alerts or reminders relating to the lifestyle protocol to include at least one of the following:
      (i) an alert relating to at least one of a lifestyle attribute, the failure of the patient to respond to one or more of the one or more queries, the response data being outside any data parameters set for the query; the response data being erroneous; and any other warning; and
      (ii) feedback or one or more reports relating to one or more lifestyle attributes and the lifestyle protocol and showing analysis or identification of trends or deterioration in relation to said one or more lifestyle attributes in accordance with the collected response data; and
   (c) analyzing the response data, identifying trends in the response data, and monitoring compliance by the patient, in accordance with the lifestyle protocol to generate the feedback or the one or more reports.

7. The method of claim 1, further comprising receiving health information associated with the patient including at least one of temperature, heart rate, glucose levels, or blood pressure results, the health information being received from the device associated with the patient.

8. The method of claim 1, further comprising receiving qualitative data associated with the patient including at least one of diet information or exercise management information, the qualitative data being received from the device associated with the patient.

9. The method of claim 1, wherein analyzing the response data further comprises at least one of:
   (a) identifying trends in the response data;
   (b) comparing the response data to one or more response parameters;

(c) identifying trends in the response data and comparing the trends to the one or more response parameters; and (d) generating an alert specific to the analysis of the response data and transmitting the alert to the device associated with the patient in accordance with the one or more schedules.

10. The method of claim 9, further comprising receiving a request from the patient to generate one or more alerts specific to particular response parameters, whereby response data above a limit in the alert and reminder threshold settings is associated with a serious condition and a critical alert, and response data below the limit in the alert and reminder threshold settings is associated with a less serious condition and a non-critical alert.

11. The method of claim 9, further comprising receiving a request from a patient choosing at least one of: one or more response parameters relating to response data or the content of the alert specific to the one or more response parameters.

12. The method of claim 1, further comprising identifying one or more patients registering similar lifestyle attributes with the monitoring scheme and facilitating chats and support amongst the identified one or more patients.

13. The method of claim 1, wherein receiving response data from the device associated with the patient further comprises providing the patient with an incentive related to a telecommunications company providing service for the personal communication device.

14. The method of claim 1, wherein receiving response data from the personal communication device further comprises providing the patient with an incentive related to a healthcare provider providing service to the patient. 09oijh.

15. A computerized system for monitoring patient health using a patient-managed monitoring scheme, the system being configured to manage a patient account associated with a patient and an administrator account associated with an administrator of the patient, the system comprising:

a memory storing instructions; and at least one processor configured to execute the stored instructions to perform operations including:

providing a patient interface configured to authenticate a patient and enable communication between the patient and the server during a patient-authenticated session on the patient account;

providing an administration interface configured to authenticate an administrator and enable communication between the administrator and the server during an administrator-authenticated session on the administrator account;

receiving, from a device associated with the patient account, a proposed monitoring scheme including settings for notifications and monitoring parameters manually selected during the patient-authenticated session on the patient account;

providing, by the server, an indication of the proposed monitoring scheme to a device associated with the administrator account;

receiving approval information from the device associated with the administrator account, the approval information including an approval indication of the proposed monitoring scheme input during the administrator-authenticated session on the administrator account;

based on the approval information, updating a database entry associated with the patient account and activating the proposed monitoring scheme;

generating instructions for monitoring quantitative and qualitative data based on the settings for notifications and monitoring parameters, wherein the settings for notifications and monitoring parameters include:

one or more messages chosen or manually-created during the patient-authenticated session, the one or more messages including personalized queries for lifestyle attributes, one or more alert and reminder threshold settings for alerts and reminders defined to be sent in relation to at least one of response data associated with a query sent to the device associated with the patient account, a schedule, or specific events, and one or more schedules for providing the personalized queries to the patient;

sending at least one query to the device associated with the patient account, based on the personalized queries chosen or manually created during the patient-authenticated session;

one of:

receiving response data from the device associated with the patient account, or generating response data indicating a lack of a response from the device associated with the patient;

analyzing the response data based on the one or more alert and reminder threshold settings;

choosing at least one alert or reminder from the settings, based on at least one of the one or more schedules or the analysis of the received response data; and transmitting the chosen alert or reminder to at least one of the device associated with the patient account or one or more other devices associated with one or more other third parties.

16. The system of claim 15, wherein, at least one of the personalized queries requires response data that is within an acceptable range of values defined by the alert or reminder threshold settings for the lifestyle attribute, and the one or more alerts or reminders are transmittable to the patient or the other persons in accordance with the settings for notifications and monitoring parameters, to alert or remind the patient or optionally the other persons of any of the following:

a lack of response by the patient to one or more queries, and response data outside set parameters for the one or more queries;

results of analysis of the response data to identify trends relating to one or more of the lifestyle attributes; or feedback for the patient and optionally the other persons, in accordance with the one or more notification settings, said feedback relating to the identified trends or the compliance of the response data with one or more lifestyle management standards or parameters, such feedback being provided as one or more notifications.

17. The system of claim 15, further comprising a telephony server in communication with the at least one processor and operable to:

support a connection between one or more personal communication devices and the at least one processor; and/or support an Internet connection between one or more personal communication devices and the at least one processor.

18. The system of claim 17, wherein the one or more devices associated with the patient comprise at least one of: a personal computer; a cellular phone; one or more health sensors for measuring at least one of temperature, blood pressure, and heart rate; a smart phone; a short-range wireless device; and a cellular phone having one or more health sensors embedded therein.

19. The system of claim 15, wherein sending the at least one query comprises transmitting one or more text messages.

20. The system of claim 15, wherein the at least one processor is linked to a database, and includes a database management utility operable to manage the storage and retrieval of response data in the database, said database management utility being operable to encrypt the response data provided by the patient.

21. The system of claim 15, wherein the patient interface includes at least one of the following:
   (a) one or more web pages defining the patient interface;
   (b) a patient account login page;
   (c) notification scheme setup page including notification content creation and selection means for selecting notification content that includes a selection means for selecting at least one of one or more lifestyle attributes, one or more intervals or one or more input selections;
   (d) a database access page including a response data input means for inputting response data, a data review means for inputting data reviews, a notification scheme modification means for inputting notification scheme modifications, and a data printing means for inputting data printing commands; and
   wherein the administration interface includes:
   (a) an administrator login page to access the administration interface; and
   (b) an administrator approval request page.

22. The system of claim 15, wherein the device associated with the patient is operable to do any of the following:
   (a) incorporate, or be linked to, one or more sensors operable for wireless communication and relating to one or more of the one or more lifestyle attributes, said one or more sensors including at least one of a glucometer, a heart rate monitor, a blood pressure monitor; a distance monitor, a global positioning system; or any other lifestyle or health attribute monitor;
   (b) generate and transmit response data as one or more of a text message or a voice-activated response; and
   (c) receive the one or more notifications as at least one of a text message, an voice alert, a musical alert, a ring tone, a specific sound produced by the personal communication device, an instant message, an email, a link to one or more websites, phone numbers, or suppliers relevant to the notification, or a communication link to any health provider or the other persons via text, cell, email, web, video or other connection.

23. The system of claim 15 wherein the response data comprises information including one or more of glucose levels or blood pressure.

24. The system of claim 15, wherein the response data comprises qualitative data relevant to diet or exercise management.

25. A system of claim 15, wherein the at least one processor is configured to perform at least one of reminder generation, bulk messaging, account review, administrator compliance review, patient group reminder review, unique patient reminder review, glucose level review, blood pressure review, medication usage review, patient created reminder creation and modification, administration created reminder creation and modification, administration interface event log, compliance review response, or patient report module.

26. A non-transitory computer readable medium storing instructions that, when executed, configure at least one processor to perform a computerized method of monitoring patient health using a patient-managed monitoring scheme, the at least one processor being configured to manage a patient account associated with a patient and an administrator account associated with an administrator of the patient, the method comprising:
   providing a patient interface configured to authenticate a patient and enable communication between the patient and the server during a patient-authenticated session on the patient account;
   providing an administration interface configured to authenticate an administrator and enable communication between the administrator and the server during an administrator-authenticated session on the administrator account;
   receiving, from a device associated with the patient account, a proposed monitoring scheme including settings for notifications and monitoring parameters manually selected during the patient-authenticated session on the patient account;
   providing, by the server, an indication of the proposed monitoring scheme to a device associated with the administrator account;
   receiving approval information from the device associated with the administrator account, the approval information including an approval indication of the proposed monitoring scheme input during the administrator-authenticated session on the administrator account;
   based on the approval information, updating a database entry associated with the patient account and activating the proposed monitoring scheme;
   generating instructions for monitoring quantitative and qualitative data based on the settings for notifications and monitoring parameters, wherein the settings for notifications and monitoring parameters include:
      one or more messages chosen or manually-created during the patient-authenticated session, the one or more messages including personalized queries for lifestyle attributes,
      one or more alert and reminder threshold settings for alerts and reminders defined to be sent in relation to at least one of response data associated with a query sent to the device associated with the patient account, a schedule, or specific events, and
      one or more schedules for providing the personalized queries to the patient;
   sending at least one query to the device associated with the patient account, based on the personalized queries chosen or manually created during the patient-authenticated session;
   one of:
      receiving response data from the device associated with the patient account, or
      generating response data indicating a lack of a response from the device associated with the patient;
   analyzing the response data based on the one or more alert and reminder threshold settings;
   choosing at least one alert or reminder from the settings, based on at least one of the one or more schedules or the analysis of the received response data; and
   transmitting the chosen alert or reminder to at least one of the device associated with the patient account or one or more other devices associated with one or more other third parties.

27. A computerized method of providing a patient health service based on a patient-managed monitoring scheme, the method comprising:
  hosting, by a server, a lifestyle self-management system, by:
    managing a patient account associated with a patient and an administrator account associated with an administrator of the patient;
    providing a patient interface configured to authenticate a patient and enable communication between the patient and the server during a patient-authenticated session on the patient account;
    providing an administration interface configured to authenticate an administrator and enable communication between the administrator and the server during an administrator-authenticated session on the administrator account;
    receiving, from a device associated with the patient account, a proposed monitoring scheme including settings for notifications and monitoring parameters manually selected during the patient-authenticated session on the patient account;
    providing, by the server, an indication of the proposed monitoring scheme to a device associated with the administrator account;
    receiving approval information from the device associated with the administrator account, the approval information including an approval indication of the proposed monitoring scheme input during the administrator-authenticated session on the administrator account;
    based on the approval information, updating a database entry associated with the patient account and activating the proposed monitoring scheme;
    generating instructions for monitoring quantitative and qualitative data based on the settings for notifications and monitoring parameters, wherein the settings for notifications and monitoring parameters include:
      one or more messages chosen or manually-created during the patient-authenticated session, the one or more messages including personalized queries for lifestyle attributes,
      one or more alert and reminder threshold settings for alerts and reminders defined to be sent in relation to at least one of response data associated with a query sent to the device associated with the patient account, a schedule, or specific events, and
      one or more schedules for providing the personalized queries to the patient;
    sending at least one query to the device associated with the patient account, based on the personalized queries chosen or manually created during the patient-authenticated session;
    one of:
      receiving response data from the device associated with the patient account, or
      generating response data indicating a lack of a response from the device associated with the patient;
    analyzing the response data based on the one or more alert and reminder threshold settings;
    choosing at least one alert or reminder from the settings, based on at least one of the one or more schedules or the analysis of the received response data; and
    transmitting the chosen alert or reminder to at least one of the device associated with the patient account or one or more other devices associated with one or more other third parties;
  partnering the lifestyle self-management system with at least one telecommunications or healthcare provider server;
  providing, by the telecommunications or healthcare provider server, a subscription-based service associated with the lifestyle self-management system;
  collecting, by the telecommunications or healthcare provider server, subscription fees from the patient.

28. A computerized method of monitoring patient health and compliance using a patient-managed monitoring scheme, the method being performed by a server configured to manage a patient account associated with a patient and an administrator account associated with an administrator of the patient, the method comprising:
  receiving, from a device associated with the patient account, a proposed monitoring scheme including settings for notifications and monitoring parameters manually selected during the patient-authenticated session on the patient account, wherein the proposed monitoring scheme is received from a patient interface configured to authenticate a patient and enable communication between the patient and the server during a patient-authenticated session on the patient account
  receiving approval information from the device associated with the administrator account, the approval information including an approval indication of the proposed monitoring scheme input during the administrator-authenticated session on the administrator account, wherein the approval information is received from an administration interface configured to authenticate an administrator and enable communication between the administrator and the server during an administrator-authenticated session on the administrator account;
  based on the approval information, updating a database entry associated with the patient account and activating the proposed monitoring scheme;
  generating instructions for monitoring quantitative and qualitative data based on the settings for notifications and monitoring parameters, wherein the settings for notifications and monitoring parameters include:
    one or more messages chosen or manually-created during the patient-authenticated session, the one or more messages including personalized queries for lifestyle attributes,
    one or more alert and reminder threshold settings for alerts and reminders defined to be sent in relation to at least one of response data associated with a query sent to the device associated with the patient account, a schedule, or specific events, and
    one or more schedules for providing the personalized queries to the patient;
  sending at least one query to the device associated with the patient account, based on the personalized queries chosen or manually created during the patient-authenticated session;
  one of:
    receiving response data from the device associated with the patient account, or
    generating response data indicating a lack of a response from the device associated with the patient;
  analyzing the response data based on the one or more alert and reminder threshold settings;

choosing at least one alert or reminder from the settings, based on at least one of the one or more schedules or the analysis of the received response data; and transmitting the chosen alert or reminder to at least one of the device associated with the patient account or one or more other devices associated with one or more other third parties.

* * * * *